(12) United States Patent
Pitterna et al.

(10) Patent No.: US 7,678,740 B2
(45) Date of Patent: *Mar. 16, 2010

(54) AVERMECTIN AND AVERMECTIN MONOSACCHARIDE DERIVATIVES SUBSTITUTED IN THE 4"-OR 4'-POSITION HAVING PESTICIDAL PROPERTIES

(75) Inventors: Thomas Pitterna, Basel (CH); Fiona Murphy Kessabi, Basel (CH); Peter Maienfisch, Basel (CH); Jerome Cassayre, Basel (CH); Laura Quaranta, Basel (CH); Pierre Jung, Basel (CH)

(73) Assignee: Merial Limited, Duluth, GA (US)

( * ) Notice: Subject to any disclaimer, the term of this patent is extended or adjusted under 35 U.S.C. 154(b) by 104 days.

This patent is subject to a terminal disclaimer.

(21) Appl. No.: 10/543,637

(22) PCT Filed: Jan. 30, 2004

(86) PCT No.: PCT/EP2004/000890

§ 371 (c)(1),
(2), (4) Date: Jul. 28, 2005

(87) PCT Pub. No.: WO2004/067543

PCT Pub. Date: Aug. 12, 2004

(65) Prior Publication Data
US 2006/0140997 A1   Jun. 29, 2006

(30) Foreign Application Priority Data
Jan. 31, 2003  (GB) ................. 0302308.2

(51) Int. Cl.
A01N 25/26 (2006.01)
A01N 43/02 (2006.01)
A01N 43/04 (2006.01)
C07H 17/08 (2006.01)

(52) U.S. Cl. ............... 504/100; 504/291; 514/28; 536/7.1

(58) Field of Classification Search ........... 514/183, 514/28; 504/100, 291; 536/7.1
See application file for complete search history.

(56) References Cited

U.S. PATENT DOCUMENTS

| | | | |
|---|---|---|---|
| 4,203,976 A | 5/1980 | Fisher et al. | |
| 4,206,205 A | 6/1980 | Mrozik et al. | |
| 4,427,663 A | 1/1984 | Mrozik et al. | |
| 4,622,313 A | 11/1986 | Wyvrath, Jr. et al. | |
| 4,831,016 A | 5/1989 | Mrozik et al. | |
| 4,895,837 A | 1/1990 | Mrozik et al. | |
| 5,023,241 A | 6/1991 | Linn et al. | |
| 5,057,499 A | 10/1991 | Mrozik et al. | |
| 5,169,839 A | 12/1992 | Linn et al. | |
| 5,192,546 A | 3/1993 | Abercrombie et al. | |
| 5,208,222 A | 5/1993 | Meinke et al. | |
| 5,229,415 A | 7/1993 | Linn et al. | |
| 5,346,698 A | 9/1994 | Abercrombie et al. | |
| 5,362,863 A | 11/1994 | Cvetovich et al. | |
| 5,436,355 A | 7/1995 | Demchak et al. | |
| 5,945,445 A | 8/1999 | Barringer et al. | |
| 5,981,500 A | 11/1999 | Bishop et al. | |
| 6,605,595 B1 | 8/2003 | Omura et al. | |
| 6,875,727 B2 | 4/2005 | Hofer et al. | |
| 6,933,260 B2 | 8/2005 | Cassayre | |
| 7,250,402 B2 | 7/2007 | Omura et al. | |

(Continued)

FOREIGN PATENT DOCUMENTS

EP   001688   5/1979

(Continued)

OTHER PUBLICATIONS

U.S. Appl. No. 10/568,715, filed Feb. 17, 2006, Kasaba et al.

(Continued)

*Primary Examiner*—Alton N Pryor
(74) *Attorney, Agent, or Firm*—Judy Jarecki-Black; Thomas Kowalski; Merial Limited

(57) ABSTRACT

What is described are a compound of the formula (I) Wherein U is —N($R_2$)$OR_3$ or —N$^+$(O$^-$)=C($R_E$)$R_Z$); n is 0 or 1; X—Y is —CH=CH— or —CH$_2$—CH$_2$—; $R_1$ is $C_1$-$C_{12}$alkyl, $C_3$-$C_8$cycloalkyl or $C_2$-$C_{12}$alkenyl; $R_2$ and $R_3$ are, for example; independently from each other, —Q, —C(=O)—Z—Q or —CN; $R_Z$ and $R_E$ are, independently from each other, —Q, —C(=O)—Z—Q or —CN; or $R_Z$ and $R_E$ together are a three- to seven membered alkylene or alkenylene bridge, which is unsubstituted or mono- to tri-substituted; Z is a bond, O or —NR$_4$—; Q is H, $C_1$-$C_{12}$alkyl, $C_2$-$C_{12}$alkenyl, $C_2$-$C_{12}$alkynyl, $C_3$-$C_{12}$-Cycloalkyl, $C_5$-$C_{12}$-cycloalkenyl, aryl, or heterocyclyl, which are unsubstituted or mono- to pentasubstituted; $R_4$ is for example H, $C_1$-$C_8$alkyl, hydroxy-$C_1$-$C_8$alkyl, $C_3$-$C_8$cycloalkyl or $C_2$-$C_8$alkenyl; or, if appropriate, an E/Z isomer, E/Z isomer mixture and/or tautomer thereof; a process for preparing these compounds, their isomers and tautomers and the use of these compounds, their isomers and tautomers; pesticidal compositions whose active compound is selected from these compounds and their tautomers; intermediates for the preparation of the said compounds of the formula (I), methods for the preparation of the compounds of the formula (I), and a method for controlling pests using these compositions.

(I)

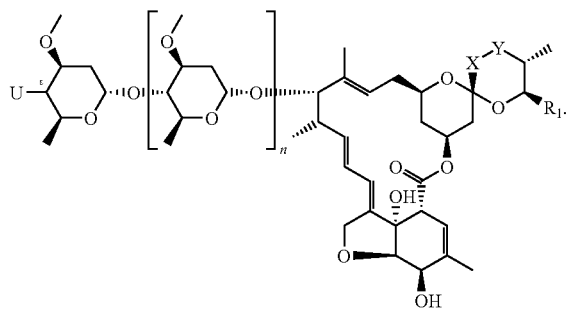

6 Claims, No Drawings

U.S. PATENT DOCUMENTS

| | | | |
|---|---|---|---|
| 7,378,399 | B2 | 5/2008 | Cassayre et al. |
| 2006/0140997 | A1 | 6/2006 | Pitterna et al. |
| 2006/0205595 | A1* | 9/2006 | Pitterna et al. ............... 504/100 |
| 2008/0051353 | A1* | 2/2008 | Jung et al. .................... 514/30 |

FOREIGN PATENT DOCUMENTS

| | | |
|---|---|---|
| EP | 0089202 | 9/1983 |
| EP | 0259688 | 3/1988 |
| EP | 0266131 | 5/1988 |
| EP | 0301806 | 1/1989 |
| EP | 0340849 | 11/1989 |
| EP | 0343708 | 11/1989 |
| EP | 0375393 | 6/1990 |
| EP | 375393 * | 6/1990 |
| EP | 0411897 | 6/1991 |
| EP | 0456509 | 11/1991 |
| EP | 0465121 | 1/1992 |
| EP | 0506331 | 9/1992 |
| EP | 0519731 | 12/1992 |
| EP | 1160252 | 12/2001 |
| WO | WO 93/15099 | 8/1993 |
| WO | WO 95/20877 | 8/1995 |
| WO | WO 96/22300 | 7/1996 |
| WO | WO 02/068441 | 9/2002 |
| WO | WO 02/068442 | 9/2002 |
| WO | WO 03/020738 | 3/2003 |
| WO | WO 03020738 * | 3/2003 |
| WO | WO 03/053988 | 7/2003 |
| WO | WO 2004/067534 | 8/2004 |

OTHER PUBLICATIONS

U.S. Appl. No. 10/560,390, filed Mar. 22, 2006, Pitterna et al.
U.S. Appl. No. 10/544,274, filed Aug. 3, 2005, Cassayare et al.
U.S. Appl. No. 10/544,281, filed Aug. 3, 2005, Quaranta et al.
U.S. Appl. No. 10/543,638, filed Jul. 28, 2005, Pitterna et al.
U.S. Appl. No. 10/543,643, filed Apr. 5, 2006, Pitterna et al.
U.S. Appl. No. 10/513,247, filed Nov. 2, 2004, Tobler et al.
U.S. Appl. No. 10/498,858, filed Jun. 14, 2004, Cassayare et al.
U.S. Appl. No. 10/488,225, filed Feb. 26, 2004, Tobler et al.
U.S. Appl. No. 11/319,686, filed Dec. 28, 2005, Pitterna et al.
U.S. Appl. No. 11/319,687, filed Dec. 28, 2005, Pitterna et al.
U.S. Appl. No. 10/539,274, filed Mar. 9, 2006, Maienfisch et al.
Fisher, American Chemical Society Symposium, 1997, vol. 658, Phytochemicals for Pest Control.
J. Med. Chem. 1992, 35, 3879-3884; "Affinity Probes for the Avermectin Binding Proteins".
Jones, T K et al.; "Synthesis and Biological Activity of 4a,4-Disubstituted Avermectins"; Journal of Agriculture and Food Chemistry, American Chemical Society, 42 1994, p. 1786-1790.
Meinke et al.; "Synthesis of Avermectin B1-4',4'a -Oxide: A Precursor to Potent Anthelmintic Agents", Biorganic Medicinal Chemistry Letters, vol. 2, 1992 p. 537.
Mrozik, H et al.; "Avermectin Acyl-Derivatives with Anthelmintic Activity". Journal of Medicinal Chemistry, Vol. 25, 1982, pp. 658-663.
Mrozik et.al.; 4 Deoxy-4-Aminoavermectins With Potent Broad Spectrum Antiparasitic Activities. Bioorganic and Medicinal Chem. Letts. vol. 5, No. 20, 1995, pp. 2435-2440.
Shoop et al.; Efficacy in Sheep and Pharmacokinetics in Cattle that Led to the Selection of Eprinomectin as a Topical Endectocide for Cattle, International Journal for Parasitology, 1996, 26 (11), 1227-1235.
Wrzesinski et al; Journal of Agricultural and Food Chemistry, vol. 44, 1996, pp. 304-312.
Yoshii et al.; Simultaneous Determination of Residues of Emamectin and Its Metabolites, and Milbemectin, Ivermectin, and Abamectin in Crops by Liquid Chromatography with Fluorescence Detection. Journal of AOAC International vol. 84, No. 3, pp. 910-917.
Cvetovich, et al.; "Synthesis of 4"-epi-Amino-4"-deoxyavermectins B1", J. Org. Chem, 1994, 59, pp. 7704-7708.
Fisher, M.H. "Phytochemicals for Pest Control", American Chemical Society Symposium, 1997, vol. 658, 220-238.
Meinke, P., et al. "Affinity Probes for the Avermectin Binding Protiens" J. Med. Chem. 1992, 35, 3879-3884.
Jones, T K et al.; "Synthesis and Biological Activity of 4a, 4-Disubstituted Avermectins", Journal of Agriculture and Food Chemistry, American Chemical Society, 42 1994, p. 1786-1790.
Meinke et al.,; "Synthesis of Avermectin B1-4', 4'a -Oxide: A Precursor to Potent Anthelmiatic Agents", Biorganic Medicinal Chemistry Letters, vol. 2, 1992 p. 537.
Mrozik, H et al.; "Avermectin Acyl-Derivatives with Anthelmintic Activity", Journal of Medicinal Chemistry, vol. 25, 1982, pp. 658-663.
Mrozik et al.; 4 Deoxy-4-Aminoavermectins With Potent Spectrum Antiparasitic Activities. Bioorganic and Medicinal Chem. Lett. vol. 5. No. 20. 1995, pp. 2435-2440.
Shoop et al., Efficacy in Sheep and Pharmacokinetics in Cattle that Led to the Selection of Eprinomectin as a Topical Endectocide for Cattle, International Journal for Parasitology, 1996, 26(11), 1227-1235.
Wrzesinski et al; "Isolation and Identification of Residues of 4"-(epi-Methylamino)-4"-deoxyavermectin B1a Benzoate from the Surface of Cabbage", Journal of Agricultural and Food Chemistry, vol. 44, 1996, pp. 304-312.
Yoshii et al., "Simultaneous Determination of Residues of Emamectin and Its Metabolites, and Milbemectin. Ivermectin, and Adamectin in Crops by Liquid Chromatography with Fluorescence Detection", Journal of AOAC International vol. 84, No. 3, pp. 910-917.

* cited by examiner

AVERMECTIN AND AVERMECTIN MONOSACCHARIDE DERIVATIVES SUBSTITUTED IN THE 4"-OR 4'-POSITION HAVING PESTICIDAL PROPERTIES

This application is a 371 of International Application No. PCT/EP2004/000890 filed Jan. 30, 2004, which claims priority to GB 0302308.2, filed Jan. 31, 2003, the contents of which are incorporated herein by reference.

The invention relates (1) to compound of the formula (I)

wherein

U is —N($R_2$)O$R_3$ or —N$^+$(O$^-$)=C($R_E$)$R_Z$);

n is 0 or 1;

X—Y is —CH=CH— or —CH$_2$—CH$_2$—;

$R_1$ is $C_1$-$C_{12}$alkyl, $C_3$-$C_8$cycloalkyl or $C_2$-$C_{12}$alkenyl;

$R_2$ and $R_3$ are, independently from each other, —Q, —C(=O)—Z—Q or —CN; or $R_2$ and $R_3$ together are a three- to seven membered alkylene or alkenylene bridge, which is unsubstituted or mono to trisubstituted;

$R_Z$ and $R_E$ are, independently from each other, —Q, —C(=O)—Z—Q or —CN; or $R_Z$ and $R_E$ together are a three- to seven membered alkylene or alkenylene bridge, which is unsubstituted or mono to trisubstituted;

Z is a bond, O or —N$R_4$—;

$R_4$ is H, $C_1$-$C_8$alkyl, hydroxy-$C_1$-$C_8$alkyl, $C_3$-$C_8$cycloalkyl, $C_2$-$C_8$alkenyl, $C_2$-$C_8$alkynyl, phenyl, benzyl —C(=O)$R_5$, or —CH$_2$—C(=O)—$R_5$;

Q is H, $C_1$-$C_{12}$alkyl, $C_2$-$C_{12}$alkenyl, $C_2$-$C_{12}$alkynyl, $C_3$-$C_{12}$-cycloalkyl, $C_5$-$C_{12}$-cycloalkenyl, aryl, or heterocyclyl, which are unsubstituted or mono- to pentasubstituted;

wherein the alkyl-, alkenyl-, alkynyl-, alkylene-, alkenylene-, cycloalkyl-, cycloalkenyl-, aryl- and heterocyclyl-radicals of the substituents Q, $R_2$, $R_3$, $R_4$, $R_Z$, $R_E$ and Q are independently of each other selected from the group consisting of OH, =O, SH, =S, halogen, CN, —N$_3$, SCN, NO$_2$, Si($C_1$-$C_8$alkyl)$_3$, halo-$C_1$-$C_2$alkyl, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_2$-$C_{12}$alkenylthio, $C_2$-$C_{12}$halo-alkenylthio, $C_2$-$C_{12}$alkenylsulfinyl, $C_2$-$C_{12}$haloalkenylsulfinyl, $C_2$-$C_{12}$alkenylsulfonyl, $C_2$-$C_{12}$haloalkenylsulfonyl, $C_3$-$C_8$cycloalkyl which is unsubstituted or substituted by one to three methyl groups, norbornylenyl, $C_3$-$C_8$halocycloalkyl, $C_1$-$C_{12}$alkoxy, $C_3$-$C_8$cycloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cyclo-alkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, —N($R_8$)$_2$ wherein the two $R_8$ are independent of each other, —C(=O)$R_5$, —O—C(=O)$R_6$, —NHC(=O)$R_5$, —S—C(=S)$R_6$, —P(=O)(O$C_1$-$C_6$alkyl)$_2$, —S(=O)$_2$$R_9$; —NH—S(=O)$_2$$R_9$, OC(=O)—$C_1$-$C_6$alkyl-S(=O)$_2$$R_9$, aryl, benzyl, heterocyclyl, aryloxy, benzyloxy, heterocyclyloxy, arylthio, benzylthio, heterocyclylthio; wherein the aryl, heterocyclyl, aryloxy, benzyloxy, heterocyclyloxy, arylthio, benzylthio and heterocyclylthio radicals are either unsubstituted or, depending on the possibilities of substitution on the ring, mono- to pentasubstituted by substituents selected from the group consisting of OH, halogen, CN, NO$_2$, $C_1$-$C_{12}$alkyl, $C_1$-$C_{12}$haloalkyl, Si($C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_3$-$C_8$cycloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl, methylenedioxy, —C(=O)$R_5$, —O—C(=O)—$R_6$, —NH—C(=O)$R_6$, —N($R_8$)$_2$, wherein the two $R_8$ are independent of each other, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

$R_5$ is H, OH, SH, —N($R_8$)$_2$ wherein the two $R_8$ are independent of each other, $C_1$-$C_{24}$alkyl, $C_2$-$C_{12}$alkenyl, $C_1$-$C_8$hydroxyalkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkyl, $C_1$-$C_6$alkoxy- $C_1$-$C_6$alkoxy, $C_1$-$C_6$alkoxy-$C_1$-$C_6$alkoxy-$C_1$-$C_6$alkyl, $C_1$-$C_{12}$alkylthio, $C_2$-$C_8$alkenyloxy, $C_3$-$C_8$alkynyloxy, Si($C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, NH—$C_1$-$C_6$alkyl-C(=O)R$_7$, —N($C_1$-$C_6$alkyl)-$C_1$-$C_6$alkyl-C(=O)—R$_7$, —O—$C_1$-$C_2$alkyl-C(=O)R$_7$, —$C_1$-$C_6$alkyl-S(=O)$_2$R$_9$, aryl, benzyl, heterocyclyl, aryloxy, benzyloxy, heterocyclyloxy; or aryl, benzyl, heterocyclyl, aryloxy, benzyloxy or heterocyclyloxy; which are independently of one another, depending on the substitution possibilities, mono- to trisubstituted in the ring by halogen, nitro, $C_1$-$C_6$alkyl, $C_1$-$C_6$alkoxy, $C_1$-$C_6$haloalkyl or $C_1$-$C_6$haloalkoxy;

R$_6$ is H, $C_1$-$C_{24}$alkyl, $C_1$-$C_{12}$haloalkyl, $C_1$-$C_{12}$hydroxyalkyl, $C_2$-$C_8$alkenyl, $C_2$-$C_8$alkynyl, $C_1$-$C_6$alkoxy-$C_1$-$C_6$alkyl, Si($C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$Cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, (NR$_8$)$_2$, wherein the two R$_8$ are independent of each other, —$C_1$-$C_6$alkyl-C(=O)R$_8$, —$C_1$-$C_6$alkyl-S(=O)$_2$R$_9$, aryl, benzyl, heterocyclyl; or aryl, benzyl or heterocyclyl which, depending on the possibilities of substitution on the ring, are mono- to trisubstituted by substituents selected from the group consisting of OH, halogen, CN, NO$_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, Si($C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy and $C_1$-$C_{12}$haloalkylthio;

R$_7$ is H, OH, $C_1$-$C_{24}$alkyl that is optionally substituted with OH, or —S(=O)$_2$—$C_1$-$C_6$alkyl; $C_1$-$C_{12}$alkenyl, $C_2$-$C_{12}$alkynyl, $C_1$-$C_{12}$alkoxy, $C_1$-$C_6$ alkoxy-$C_1$-$C_6$alkyl, $C_1$-$C_6$alkoxy-$C_1$-$C_6$alkoxy, $C_2$-$C_8$alkenyloxy, aryl, aryloxy, benzyloxy, heterocyclyl, heterocyclyloxy or —N(R$_8$)$_2$, wherein the two R$_8$ are independent of each other;

R$_8$H, $C_1$-$C_6$alkyl, which is optionally substituted with one to five substituents selected from the group consisting of halogen, hydroxy, cyano $C_1$-$C_6$alkoxy, =O, $C_2$-$C_{12}$alkenyl, $C_2$-$C_{12}$haloalkenyl, $C_2$-$C_{12}$haloalkynyl and $C_3$-$C_{12}$haloalkynyloxy; $C_3$-$C_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, NO$_2$, $C_1$-$C_{12}$alkyl, $C_1$-$C_{12}$haloalkyl, $C_1$-$C_{12}$alkoxy, $C_1$-$C_{12}$haloalkoxy, Si($C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_1$-$C_{12}$alkylthio and $C_1$-$C_{12}$haloalkylthio;

R$_9$ is H, $C_1$-$C_6$alkyl, which is optionally substituted with one to five substituents selected from the group consisting of halogen, $C_1$-$C_6$alkoxy, OH, =O, $C_2$-$C_{12}$alkenyl, $C_2$-$C_{12}$haloalkenyl, $C_2$-$C_{12}$haloalkynyl, $C_2$-$C_{12}$haloalkynyl and cyano; aryl, benzyl, heteroaryl; or aryl, benzyl or heteroaryl, which, depending on the possibilities of substitution on the ring, are mono- to trisubstituted by substituents selected from the group consisting of OH, halogen, CN, NO$_2$, $C_1$-$C_{12}$alkyl, $C_1$-$C_{12}$haloalkyl, Si($C_1$-$C_8$alkyl)$_3$, $C_1$-$C_{12}$alkoxy, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_1$-$C_{12}$alkylthio and $C_1$-$C_{12}$haloalkylthio;

or, if appropriate, an E/Z isomer, E/Z isomer mixture and/or tautomer thereof;

a process for preparing these compounds, their isomers and tautomers and the use of these compounds, their isomers and tautomers; pesticidal compositions whose active compound is selected from these compounds and their tautomers; intermediates for the preparation of the said compounds of the formula (I), methods for the preparation of the compounds of the formula (I), and a method for controlling pests using these compositions.

Hereinbefore and hereinafter, the configuration at the ε-position (4'- or 4"-position) of the compounds of the formulae (I) and (III) may be (S) as well as (R).

The literature proposes certain macrolide compounds for controlling pests. However, the biological properties of these known compounds are not entirely satisfactory, and, as a consequence, there is still a need for providing further compounds having pesticidal properties, in particular for the control of insects and representatives of the order Acarina. According to the invention, this object is achieved by providing the present compounds of the formulae (I), (II) and (III).

The compounds claimed according to the invention are derivatives of Avermectin. Avermectins are known to the person skilled in the art. They are a group of structurally closely related pesticidally active compounds which are obtained by fermenting a strain of the microorganism *Streptomyces avermitilis*. Derivatives of Avermectins can be obtained by conventional chemical syntheses.

The Avermectins which can be obtained from *Streptomyces avermitilis* are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent R$_1$ (in position 25) is a sec-butyl radical and an isopropyl radical, respectively. The number 1 in the name of the compounds means that carbon atoms 22 and 23 are linked by double bonds; the number 2 means that they are linked by a single bond and that the C atom 23 carries an OH group. The above nomenclature is adhered to in the description of the present invention to denote the specific structure type in the not naturally occurring Avermectin derivatives according to the invention which corresponds to the naturally occurring Avermectin. What is for instance claimed according to the invention are derivatives of compounds of the B1 series, in particular mixtures of derivatives of Avermectin B1, especially B1a and B1b, along with derivatives having a single bond between carbon atoms 22 and 23, and derivatives having other substituents in the 25-position, as well as the corresponding monosaccharides.

Some of the compounds of the formula (I) can be present as tautomers. Accordingly, hereinabove and hereinbelow, the compounds of the formula (I) are, if appropriate, also to be understood as including the corresponding tautomers, even if the latter are not specifically mentioned in each case.

The compounds of formula (I) and, where applicable, their tautomers can form salts, for example acid addition salts. These acid addition salts are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$-$C_4$alkanecarboxylic acids, for example acetic acid, unsaturated or saturated dicarboxylic acids, for example oxalic acid, malonic acid, maleic acid, fumaric acid or phthalic acid, hydroxycarboxylic acids, for example ascorbic acid, lactic acid, malic acid, tartaric acid or citric acid, or benzoic acid, or with organic sulfonic acids, such as unsubstituted or substituted, for example halo-substituted, $C_1$-$C_4$alkane- or aryl-sulfonic acids, for example methane- or p-toluene-sulfonic acid. Compounds of formula (I) that have at least one acidic group can furthermore form salts with bases. Suitable salts with bases are, for example, metal salts, such as alkali metal salts or alkaline earth metal salts, for example sodium, potassium or magnesium salts, or salts with ammonia or with an organic amine, such as morpholine, piperidine, pyrrolidine, a mono-, di- or tri-lower alkylamine, for example ethylamine, diethylamine, triethylamine or dimethylpropylamine, or a mono-, di- or trihydroxy-lower alkylamine, for example mono-, di- or tri-ethanolamine. Corresponding internal salts may also be formed where appropriate. The free form is preferred. Among the salts of the compounds of formula (I), the agrochemically advantageous salts are preferred. Hereinbefore and hereinafter, any reference to the free compounds of formula (I) or their salts is to be understood as including, where appropriate, also the corresponding salts or the free compounds of formula (I), respectively. The same applies to tautomers of compounds of formula (I) and salts thereof.

Unless defined otherwise, the general terms used hereinabove and hereinbelow have the meanings given below.

Unless defined otherwise, carbon-containing groups and compounds each contain from 1 up to and including 6, preferably from 1 up to and including 4, especially 1 or 2, carbon atoms.

Halogen—as a group per se and also as a structural element of other groups and compounds, such as haloalkyl, haloalkoxy and haloalkylthio—is fluorine, chlorine, bromine or iodine, in particular fluorine, chlorine or bromine, especially fluorine or chlorine.

Alkyl—as a group per se and also as a structural element of other groups and compounds, such as haloalkyl, alkoxy and alkylthio—is, in each case taking into account the number of carbon atoms contained in each case in the group or compound in question, either straight-chain, i.e. methyl, ethyl, propyl, butyl, pentyl, hexyl, heptyl or octyl, or branched, for example isopropyl, isobutyl, sec-butyl, tert-butyl, isopentyl, neopentyl or isohexyl.

Cycloalkyl—as a group per se and also as a structural element of other groups and compounds, such as, for example, of halocycloalkyl, cycloalkoxy and cycloalkylthio is, in each case taking into account the number of carbon atoms contained in each case in the group or compound in question, cyclopropyl, cyclobutyl, cyclopentyl, cyclohexyl, cycloheptyl or cyclooctyl.

Alkenyl—as a group per se and also as a structural element of other groups and compounds—is, taking into account the number of carbon atoms and conjugated or isolated double bonds contained in the group, either straight-chain, for example vinyl, allyl, 2-butenyl, 3-pentenyl, 1-hexenyl, 1-heptenyl, 1,3-hexadienyl or 1,3-octadienyl, or branched, for example isopropenyl, isobutenyl, isoprenyl, tert-pentenyl, isohexenyl, isoheptenyl or isooctenyl. Preference is given to alkenyl groups having 3 to 12, in particular 3 to 6, especially 3 or 4, carbon atoms.

Alkynyl—as a group per se and also as a structural element of other groups and compounds—is, in each case taking into account the number of carbon atoms and conjugated or isolated double bonds contained in the group or compound in question, either straight-chain, for example ethynyl, propargyl, 2-butynyl, 3-pentynyl, 1-hexynyl, 1-heptynyl, 3-hexen-1-ynyl or 1,5-heptadien-3-ynyl, or branched, for example 3-methylbut-1-ynyl, 4-ethylpent-1-ynyl, 4-methylhex-2-ynyl or 2-methylhept-3-ynyl. Preference is given to the group —$CH_2$—$C_2$-$C_{11}$alkynyl, in particular —$CH_2$—$C_2$-$C_5$alkynyl, especially —$CH_2$—$C_2$-$C_3$alkynyl.

Alkylene and alkenylene are straight-chain or branched bridge members; they are in particular —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2(CH_3)CH_2$—$CH_2$—, —$CH_2C(CH_3)_2$—$CH_2$—, —$CH_2$—CH=CH—, —$CH_2$—CH=CH—$CH_2$ or —$CH_2$—CH=CH—$CH_2$—$CH_2$—.

Halogen-substituted carbon-containing groups and compounds, such as, for example, halogen-substituted alkyl, alkenyl, alkynyl, cycloalkyl, alkoxy or alkylthio, can be partially halogenated or perhalogenated, where in the case of polyhalogenation the halogen substituents can be identical or different. Examples of haloalkyl—as a group per se and also as a structural element of other groups and compounds, such as haloalkoxy or haloalkylthio—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/or bromine, such as $CH_2CHBrCH_2Br$, $CF_2CHFCF_3$, $CH_2CF_2CF_3$, $CF(CF_3)_2$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers, mono- to undecasubstituted by fluorine, chlorine and/or bromine, such as $CF(CF_3)(CHF_2)CF_3$ or $CH_2(CF_2)_3CF_3$; and hexyl or one of its isomers, mono- to tridecasubstituted by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is in particular phenyl, naphthyl, anthracenyl, phenanthrenyl, perylenyl or fluorenyl, preferably phenyl.

Heterocyclyl is understood as being a three- to seven-membered monocyclic ring, which may be saturated or unsaturated, and that contains from one to three hetero atoms selected from the group consisting of N, O and S, especially N and S; or a bicyclic ring-system having from 8 to 14 ring atoms, which may be saturated or unsaturated, and that may contain either in only one ring or in both rings independently of one another, one or two hetero atoms selected from N, O and S.

Heterocyclyl is in particular piperidinyl, piperazinyl, oxiranyl, morpholinyl, thiomorpholinyl, pyridyl, N-oxidopyridinio, pyrimidyl, pyrazinyl, s-triazinyl, 1,2,4-triazinyl, thienyl, furanyl, dihydrofuranyl, tetrahydrofuranyl, pyranyl, tetrahydropyranyl, pyrrolyl, pyrrolinyl, pyrrolidinyl, pyrazolyl, imidazolyl, imidazolinyl, thiazolyl, isothiazolyl, triazolyl, oxazolyl, thiadiazolyl, thiazolinyl, thiazolidinyl, oxadiazolyl, phthalimidoyl, benzothienyl, quinolinyl, quinoxalinyl, benzofuranyl, benzimidazolyl, benzpyrrolyl, benzthiazolyl, indolinyl, isoindolinyl, cumarinyl, indazolyl, benzothiophenyl, benzofuranyl, pteridinyl or purinyl, which are preferably attached via a C atom; thienyl, benzofuranyl, benzothiazolyl, tetrahydropyranyl or indolyl is preferred; in particular pyridyl or thiazolyl. The said heterocyclyl radicals may preferably be unsubstituted or—depending on the substitution possibilities on the ring system—substituted by 1 to 3 substituents selected from the group consisting of halogen, =O, —OH, =S, SH, nitro, $C_1$-$C_6$alkyl, $C_1$-$C_6$hydroxyalkyl, $C_1$-$C_6$alkoxy, $C_1$-$C_6$haloalkyl, $C_1$-$C_6$haloalkoxy, phenyl, benzyl, —C(=O)—$R_6$ and —$CH_2$—C(=O)—$R_6$.

In the context of the present invention, preference is given to (2) compounds according to group (1) of the formula (I) in which $R_1$ is isopropyl or sec-butyl, preferably to those in which a mixture of the isopropyl and the sec-butyl derivative is present;

(3) compounds according to group (1) of the formula (I) in which $R_1$ is cyclohexyl;

(4) compounds according to group (1) of the formula (I) in which $R_1$ is 1-methyl-butyl;

(5) compounds according to one of the groups (1) to (4) of the formula (I) in which the configuration at the ε-position is (R);

(6) compounds according to one of the groups (1) to (4) of the formula (I) in which the configuration at the ε-position is (S);

(7) compounds according to one of the groups (1) to (6) of the formula (I) in which n is 1;

(8) compounds according to one of the groups (1) to (6) of the formula (I) in which n is 0;

(9) compounds according to one of the groups (1) to (8) of the formula (I) in which X—Y is —CH=CH—;

(10) compounds according to one of the groups (1) to (8) of the formula (I) in which X—Y is —$CH_2$—$CH_2$—;

(11) compounds according to one of the groups (1) to (10) of the formula (I) in which U is —N($R_2$)—O($R_3$)

(12) compounds according to one of the groups (1) to (10) of the formula (I) in which U is —$N^+$($O^-$)=C($R_Z$)($R_E$)

(13) compounds according to group (11) of the formula (I) in which $R_3$ is —Q, —C(=O)—Z—Q or —CN and $R_2$ is independently taken from —Q;

(14) compounds according to group (11) of the formula (I) in which $R_3$ is —Q, —C(=O)—Z—Q or —CN and $R_2$ is independently taken from —C(=O)—Z—Q;

(15) compounds according to group (11) of the formula (I) in which $R_3$ is —Q, —C(=O)—Z—Q or —CN and $R_2$ is —CN;

(16) compounds according to group (11) of the formula (I) in which $R_2$ is Q, —C(=O)—Z—Q or —CN and $R_3$ is independently taken from —Q;

(17) compounds according to group (11) of the formula (I) in which $R_2$ is —Q, —C(=O)—Z—Q or —CN and $R_3$ is independently taken from —C(=O)—Z—Q;

(18) compounds according to group (11) of the formula (I) in which $R_2$ is —Q, —C(=O)—Z—Q or —CN and $R_3$ is —CN;

(19) compounds according to one of the groups (13) to (18) of the formula (I) in which Z is a bond;

(20) compounds according to one of the groups (13) to (18) of the formula (I) in which Z is O;

(21) compounds according to one of the groups (13) to (18) of the formula (I) in which Z is —$NR_4$—;

(22) compounds according to group (11) of the formula (I) in which $R_2$ and $R_3$ together are a three membered alkylene bridge, which is unsubstituted or mono- to tri-substituted;

(23) compounds according to group (11) of the formula (I) in which $R_2$ and $R_3$ together are a four membered alkylene bridge, which is unsubstituted or mono- to tri-substituted;

(24) compounds according to group (11) of the formula (I) in which $R_2$ and $R_3$ together are a five membered alkylene bridge, which is unsubstituted or mono- to tri-substituted;

(25) compounds according to group (11) of the formula (I) in which $R_2$ and $R_3$ together are a six membered alkylene bridge, which is unsubstituted or mono- to tri-substituted;

(26) compounds according to group (11) of the formula (I) in which $R_2$ and $R_3$ together are a seven membered alkylene bridge, which is unsubstituted or mono- to tri-substituted;

(27) compounds according to group (11) of the formula (I) in which $R_2$ and $R_3$ together are a three membered alkenylene bridge, which is unsubstituted or mono- to tri-substituted;

(28) compounds according to group (11) of the formula (I) in which $R_2$ and $R_3$ together are a four membered alkenylene bridge, which is unsubstituted or mono- to tri-substituted;

(29) compounds according to group (11) of the formula (I) in which $R_2$ and $R_3$ together are a five membered alkenylene bridge, which is unsubstituted or mono- to tri-substituted;

(30) compounds according to group (11) of the formula (I) in which $R_2$ and $R_3$ together are a six membered alkenylene bridge, which is unsubstituted or mono- to tri-substituted;

(31) compounds according to group (11) of the formula (I) in which $R_2$ and $R_3$ together are a seven membered alkenylene bridge, which is unsubstituted or mono- to tri-substituted;

(32) compounds according to group (12) of the formula (I) in which $R_E$ is —Q, —C(=O)—Z—Q or —CN and $R_Z$ is independently taken from —Q;

(33) compounds according to group (12) of the formula (I) in which $R_E$ is —Q. —C(=O)—Z—Q or —CN and $R_Z$ is independently taken from —C(=O)—Z—Q;

(34) compounds according to group (12) of the formula (I) in which $R_E$ is —Q, —C(=O)—Z—Q or —ON and $R_Z$ is —ON;

(35) compounds according to group (12) of the formula (I) in which $R_Z$ is —Q, —C(=O)—Z—Q or —CN and $R_E$ is independently taken from —Q;

(36) compounds according to group (12) of the formula (I) in which $R_Z$ is Q, —C(=O)—Z—Q or —ON and $R_E$ is independently taken from —C(=O)—Z—Q;

(37) compounds according to group (12) of the formula (I) in which $R_Z$ is —Q, —C(=O)—Z—Q or —ON and $R_E$ is —CN;

(38) compounds according to one of the groups (32) to (37) of the formula (I) in which Z is a bond;

(39) compounds according to one of the groups (32) to (37) of the formula (I) in which Z is O;

(40) compounds according to one of the groups (32) to (37) of the formula (I) in which Z is —NR$_4$—;

(41) compounds according to group (12) of the formula (I) in which $R_Z$ and $R_E$ together are a three membered alkylene bridge, which is unsubstituted or mono- to tri-substituted;

(42) compounds according to group (12) of the formula (I) in which $R_Z$ and $R_E$ together are a four membered alkylene bridge, which is unsubstituted or mono- to tri-substituted;

(43) compounds according to group (12) of the formula (I) in which $R_Z$ and $R_E$ together are a five membered alkylene bridge, which is unsubstituted or mono- to tri-substituted;

(44) compounds according to group (12) of the formula (I) in which $R_Z$ and $R_E$ together are a six membered alkylene bridge, which is unsubstituted or mono- to tri-substituted;

(45) compounds according to group (12) of the formula (I) in which $R_Z$ and $R_E$ together are a seven membered alkylene bridge, which is unsubstituted or mono- to tri-substituted;

(46) compounds according to group (12) of the formula (I) in which $R_Z$ and $R_E$ together are a three membered alkenylene bridge, which is unsubstituted or mono- to tri-substituted;

(47) compounds according to group (12) of the formula (I) in which $R_Z$ and $R_E$ together are a four membered alkenylene bridge, which is unsubstituted or mono- to tri-substituted;

(48) compounds according to group (12) of the formula (I) in which $R_Z$ and $R_E$ together are a five membered alkenylene bridge, which is unsubstituted or mono- to tri-substituted;

(49) compounds according to group (12) of the formula (I) in which $R_Z$ and $R_E$ together are a six membered alkenylene bridge, which is unsubstituted or mono- to tri-substituted;

(50) compounds according to group (12) of the formula (I) in which $R_Z$ and $R_E$ together are a seven membered alkenylene bridge, which is unsubstituted or mono- to tri-substituted.

Special preference is given within the scope of the invention to the compounds of formula (I) listed in Tables A1 to A8 and in Tables 1 to 48 and, where applicable, their tautomers, their mixtures of tautomers, their E/Z isomers and mixtures of E/Z isomers.

The invention also provides a process for preparing the compounds of the formula (I) and, if appropriate, tautomers thereof, wherein (A) for the preparation of a compound of the formula (I) as defined under (1), wherein U is —NHOR$_3$ and R$_3$ has the same meanings as given under (1) for formula (I), a compound of the formula

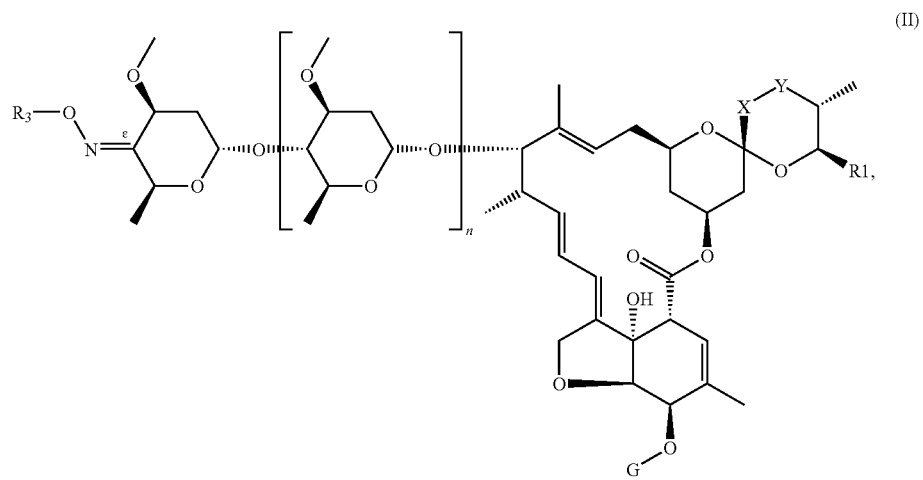

in which G is H or a protecting group, n, X—Y, $R_1$ and $R_3$ have the same meanings as given above under (1) for formula (I), is treated with a reducing agent; or
(B) for the preparation of a compound of the formula
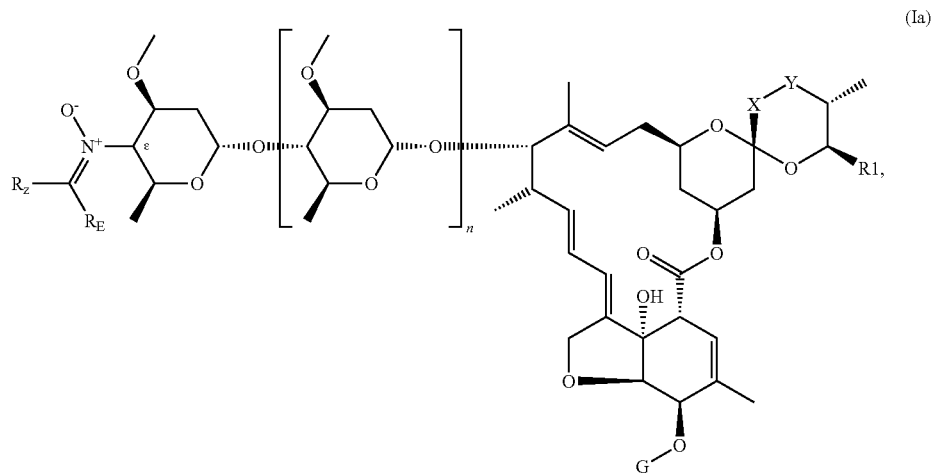
(Ia)
wherein G is H or a protecting group, n, X—Y, $R_1$, $R_E$ and $R_Z$ have the same meanings as given above under (1) for formula (I), a compound of the formula
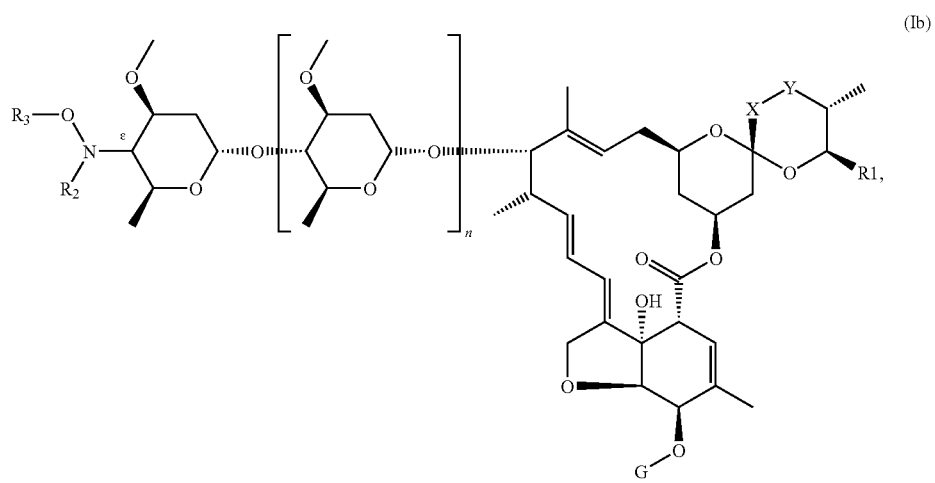
(Ib)

in which G is H or a protecting group, $R_2$ and $R_3$ are H, and n, X—Y and $R_1$ have the same meanings as given above under (1) for formula (I), is reacted with a compound of the formula $R_E$—C(=O)—$R_Z$, in which $R_E$ and $R_Z$ have the same meanings as given above under (1) for formula (I); or (C) for the preparation of a compound of the formula (Ia) as defined above under (B), a compound of the formula

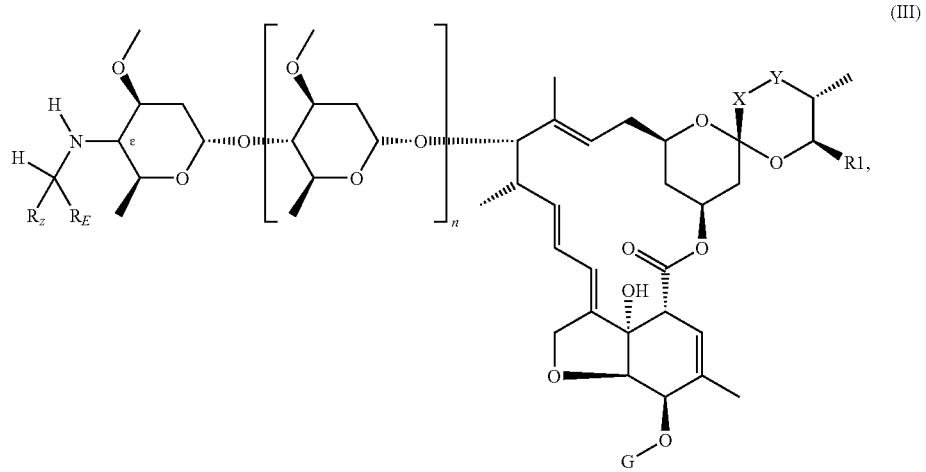

(III)

in which n, X—Y, $R_1$, $R_E$ and $R_Z$ have the same meanings as given above under (1) for formula (I), is treated with an oxidating agent; or (D) for the to preparation of a compound of the formula (Ib) as defined above under (B), wherein $R_2$ and $R_3$ are H, a compound of the formula (Ia) as defined above under (B), is reacted with a compound of the formula $Q_1$-O—$NH_2$, in which $Q_1$ is H, $C_1$-$C_{12}$alkyl, $C_2$-$C_{12}$alkenyl, $C_2$-$C_{12}$alkynyl, $C_3$-$C_{12}$cycloalkyl, $C_5$-$C_{12}$cycloalkenyl, aryl or heterocyclyl, which are unsubstituted or mono- to pentasubstituted, and wherein the substituents of the alkyl, alkenyl, alkynyl, cycloalkyl, cycloalkenyl, aryl and heterocyclyl radicals mentioned have the same meaning as given above under (1) for formula (I); or (E) for the preparation of a compound of the formula

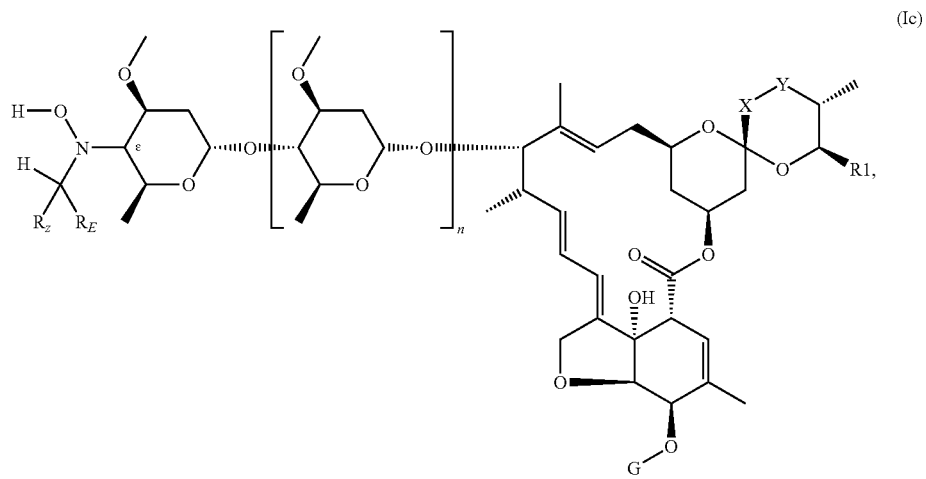

(Ic)

in which G is H or a protecting group, n, X—Y, $R_1$, $R_E$ and $R_Z$ have the same meanings as given above under (1) for formula (I), a compound of the formula (Ia) as defined above under (B) is reacted with a reducing agent; or (F) for the preparation of a compound of the formula

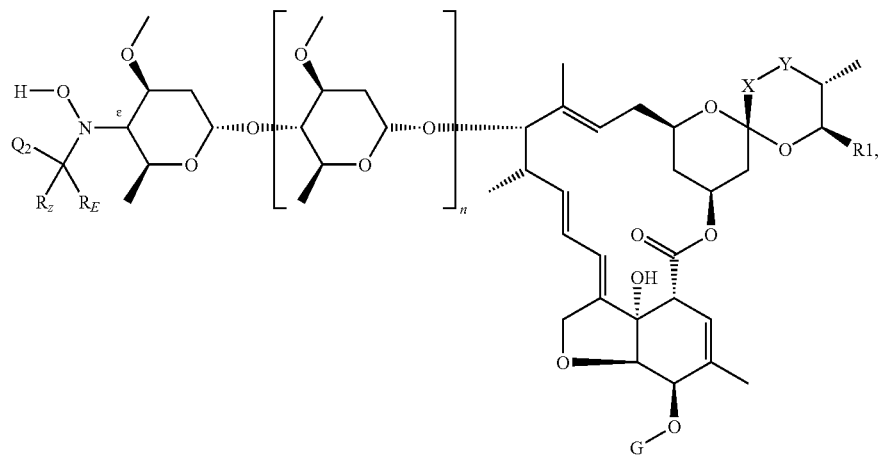

(Id)

in which G is H or a protecting group, n, X—Y, $R_1$, $R_E$ and $R_Z$ have the same meanings as given above under (1) for formula (I), and $Q_2$ is H, $C_1$-$C_{12}$alkyl, $C_2$-$C_{12}$alkenyl, $C_2$-$C_{12}$alkynyl, $C_3$-$C_{12}$cycloalkyl, $C_5$-$C_{12}$-cycloalkenyl, aryl or heterocyclyl, which are unsubstituted or mono- to penta-substituted, and wherein the substituents of the alkyl, alkenyl, alkynyl, cycloalkyl, cycloalkenyl, aryl and heterocyclyl radicals mentioned have the same meaning as given above under (1) for formula (I);

a compound of the formula (Ia) as defined above under (B) is reacted with a compound $Q_2$—M or a compound, wherein $Q_2$—M—$X_1$, both in which $Q_2$ has the same meaning as given above and M is lithium, magnesium or zinc, and $X_1$ is chloride, bromide, iodide or trifluoro-methanesulfonate; or (G) for the preparation of a compound of the formula in which G is H or a protecting group, n, X—Y, $R_1$, $R_E$ and $R_Z$ have the same meanings as given above under (1) for formula (I), and in which $Q_3$ and $Q_4$ are, independently from each other, H, $C_1$-$C_{12}$alkyl, $C_2$-$C_{12}$alkenyl, $C_2$-$C_{12}$alkynyl, $C_3$-$C_{12}$-cycloalkyl, $C_5$-$C_{12}$cycloalkenyl, aryl or heterocyclyl, which are unsubstituted or mono- to pentasubstituted, and wherein the substituents of the alkyl, alkenyl, alkynyl, cycloalkyl, cycloalkenyl, aryl and heterocyclyl radicals mentioned have the same meaning as given above under (1) for formula (I);

a compound of the formula (Ia) as defined above under (B) is reacted with a compound $Q_3$—C≡C—$Q_4$, in which $Q_3$ and $Q_4$ have the same meaning as given above; or (H) for the preparation of a compound of the formula

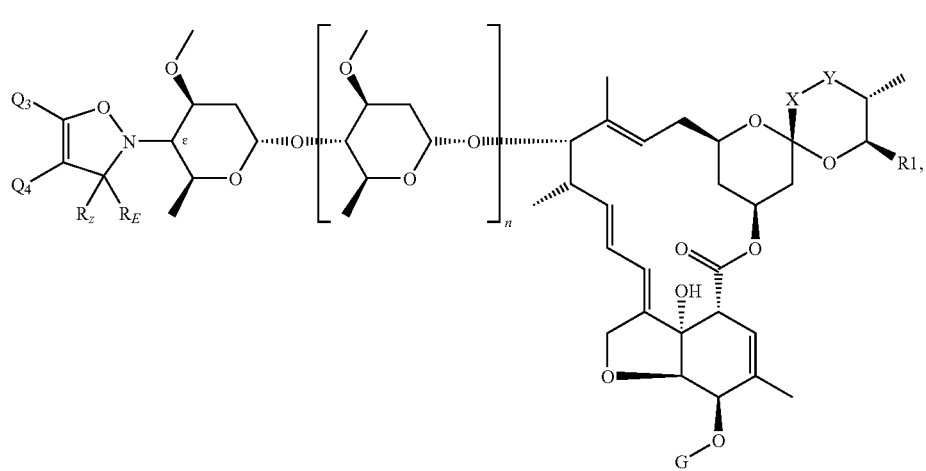

(Ie)

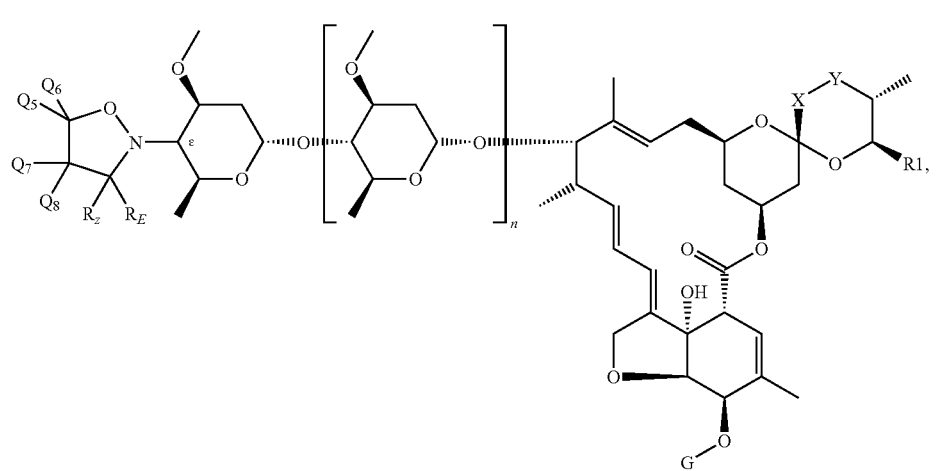

(If)

in which G is H or a protecting group, n, X—Y, $R_1$, $R_E$ and $R_Z$ have the same meanings as given above under (1) for formula (I), and in which $Q_5$, $Q_6$, $Q_7$ and $Q_8$ are, independently from each other, H, $C_1$-$C_{12}$alkyl, $C_2$-$C_{12}$alkenyl, $C_2$-$C_{12}$alkynyl, $C_3$-$C_{12}$cycloalkyl, $C_5$-$C_{12}$cycloalkenyl, aryl or heterocyclyl, which are unsubstituted or mono- to pentasubstituted, and wherein the substituents of the alkyl, alkenyl, alkynyl, cycloalkyl, cycloalkenyl, aryl and heterocyclyl radicals mentioned have the same meaning as given above under (1) for formula (I);

a compound of the formula (Ia) as defined above under (B) is reacted with a compound $Q_5Q_6C=CQ_7Q_8$, in which $Q_5$, $Q_6$, $Q_7$ and $Q_8$ have the same meaning as given above under (H) for formula (If); or (J) for the preparation of a compound of the formula (Ib) a defined above under (B), in which $R_2$ and $R_3$ have the same meanings as given above under (1) for formula (I), a compound of the formula (Ib) as defined above under (B), wherein $R_2$ is H and $R_3$ is as defined under (1) for formula (I), is reacted with a compound Q—$X_2$, with a compound Q—C(=O)—Cl, with a compound Q—O—C(=O)—Cl, with a compound Q—N=C=O or with a compound in which Q has the same meaning as given above under (1) for formula (I) and $X_2$ is chloride, bromide, iodide, alkylsulfonate, haloalkylsulfonate or arylsulfonate; or (K) for the preparation of a compound of the formula (Ib) as defined above under (B), and wherein $R_2$ and $R_3$ have the same meanings as given above under (1) for formula (I), a compound of the formula (Ib) as defined above under (B), wherein $R_2$ has the same meanings as given above under (1) for formula (I) and $R_3$ is H, is reacted with a compound Q—$X_2$, wherein $X_2$ is chloride, bromide, iodide, alkylsulfonate, haloalkylsulfonate or arylsulfonate, or with a compound Q—C(=O)—Cl, with a compound Q—O—C(=O)—Cl or with a compound Q—N=C=O, in which Q has the same meaning as given above under (1) for formula (I); or (L) for the preparation of a compound of the formula (I)

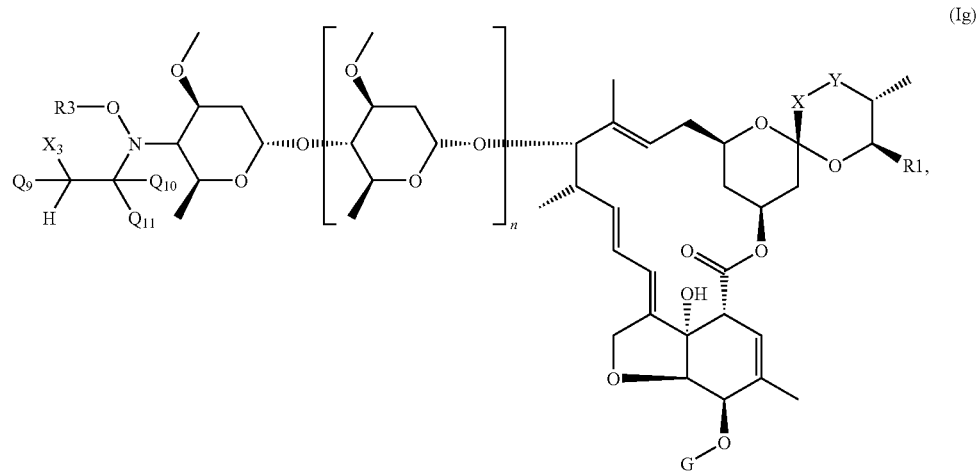

(Ig)

in which G is H or a protecting group, n, X—Y, $R_1$ and $R_3$ have the same meanings as given above under (1) for formula (I), $X_3$ is —CN or —CO—$Q_{12}$ or —CO—O—$Q_{12}$, and $Q_9$, $Q_{10}$, $Q_{11}$ and $Q_{12}$ are, independently from each other, H, $C_1$-$C_{12}$alkyl, $C_2$-$C_{12}$alkenyl, $C_2$-$C_{12}$alkynyl, $C_3$-$C_{12}$cycloalkyl, $C_5$-$C_{12}$cycloalkenyl, aryl or heterocyclyl, which are unsubstituted or mono- to pentasubstituted, and wherein the substituents of the alkyl, alkenyl, alkynyl, cycloalkyl, cycloalkenyl, aryl and heterocyclyl radicals mentioned have the same meaning as given above under (1) for formula (I);

a compound of the formula (Ib), as defined above under (B), in which $R_2$ is H and and $R_3$ has the same meanings as given above under (1) for formula (I), is reacted with a compound $Q_{10}Q_{11}C=CQ_9X_3$, in which $Q_9$, $Q_{10}$, $Q_{11}$ and $X_3$ have the same meaning as given above under (L) for formula (I);

and in each case of variants (A) to (L), if required for the synthesis of a compound of the formula (I), wherein the substituent in the 5-position is OH, the protecting group is removed.

The compounds of formulae (II) and of formula (III) are new, and are also an aspect of the invention. They are valuable intermediates for the synthesis of compounds of formula (I), and can be prepared by methods known per se. Surprisingly, they are also valuable pesticides. The use of the compounds of formula (II) and of formula (III), and of the compounds of the formula (I) having in the 5-position a protecting group, for the synthesis of compounds of formula (I), a method for controlling pests with the said compounds of the formulae (II) and (III), and pesticidal compositions containing them are also subjects of this invention. The preferences for the substituents are the same as defined for the compound of the formula (I) in (2) to (50). The compounds of the formula (I), (II) and (III) wherein the group G in the 5-position is H are preferred.

The comments made above in connection with tautomers of compounds of formula (I) apply analogously to the starting materials and intermediates mentioned hereinabove and hereinbelow in respect of their tautomers.

Compounds of formula (I) bearing a functional group in its free or protected form can be used as starting materials for the preparation of further compounds of formula (I). For such manipulations methods known to the person skilled in the art can be applied.

For example a compound of formula (I) wherein Q is $CH_2CH_2OC(=O)CH_3$ can be converted to a compound of formula (I) wherein Q is $CH_2CH_2OH$. Further standard reactions can deliver compounds of formula (I) wherein Q is —$CH_2CH_2OCH_2$-O-Alkyl or —$CH_2CH_2N_3$. A compound of formula (I) wherein Q is —$CH_2CH_2N_3$ can be converted to a compound of formula (I) wherein Q is —$CH_2CH_2NH_2$. Treatment of such a compound of formula (I) for instance with Hal-C(=O)$R_5$, gives compounds of formula (I) wherein Q is —$CH_2CH_2NHCOR_5$.

The reactions described hereinabove and hereinbelow are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Examples.

The reaction time is not critical; a reaction time of from about 0.1 to about 24 hours, especially from about 0.5 to about 10 hours, is preferred.

The product is isolated by customary methods, for example by means of filtration, crystallization, distillation or chromatography, or any suitable combination of such methods.

The starting materials mentioned hereinabove and hereinbelow that are used for the preparation of the compounds of formula (I) and, where applicable, their tautomers can be prepared by methods known per se, e.g. as indicated below.

Protecting groups G in the compounds of formulae (I), (II) and (III) include: alkyl ether radicals, such as methoxymethyl, methylthiomethyl, tert-butylthiomethyl, benzyloxymethyl, p-methoxybenzyl, 2-methoxyethoxymethyl, 2,2,2-trichloroethoxymethyl, 2-(trimethylsilyl)ethoxymethyl, tetrahydropyranyl, tetrahydrofuranyl, 1-ethoxyethyl, 1-(2-chloroethoxy)ethyl, 1-methyl-1-methoxyethyl, 1-methyl-1-benzyloxyethyl, trichloroethyl, 2-trimethylsilylethyl, tert-butyl, allyl, p-methoxyphenyl, 2,4-dinitrophenyl, benzyl, p-methoxybenzyl, o-nitrobenzyl, p-nitrobenzyl, triphenylmethyl; trialkylsilyl radicals, such as trimethylsilyl, triethylsilyl, dimethyl-tert-butylsilyl, dimethyl-isopropylsilyl, dimethyl-1,1,2-trimethylpropylsilyl, diethyl-isopropylsilyl, dimethyl-tert-hexylsilyl, but also phenyl-tert-alkylsilyl groups, such as diphenyl-tert-butylsilyl; esters, such as formates, acetates, chloroacetates, dichloroacetates, trichloroacetates, trifluoroacetates, methoxyacetates, phenoxyacetates, pivaloates, benzoates; alkyl carbonates, such as methyl-, 9-fluorenylmethyl-, ethyl-, 2,2,2-trichloroethyl-, 2-(trimethylsilyl)ethyl-, vinyl-, allyl-, benzyl-, p-methoxybenzyl-, o-nitrobenzyl-, p-nitrobenzyl-, but also p-nitrophenyl-carbonate.

Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as 9-fluorenylmethylcarbonates and allylcarbonates. Dimethyl-tert-butylsilyl ether is especially preferred.

There are suitable for the removal of the protecting group Lewis acids, such as hydrochloric acid, methanesulfonic acid, $BF_3*OEt_2$, HF in pyridine, $Zn(BF_4)_2*H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid.

Preference is given to acids, such as methanesulfonic acid or HF in pyridine; sodium borohydride with Pd(0); bases, such as ammonia, triethylamine or pyridine; especially acids, such as HF in pyridine or methanesulfonic acid.

Process Variant (A):

Examples of solvents and diluents include: aromatic, aliphatic and alicyclic hydro-carbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; alcohols, such as methanol, ethanol, propanol, isopropanol, butanol, ethylene glycol or glycerol; carboxylic acids, such as acetic acid, pivalic acid or formic acid; ketones, such as acetone, methyl ethyl ketone or methyl isobutyl ketone; carboxylic acid esters, such as methyl acetate, ethyl acetate, or esters of benzoic acid; amides, such as N,N-dimethylformamide, N, N-diethylformamide, N, N-dimethylacetamide, N-methyl-pyrrolidone or hexamethylphosphoric acid triamide; nitriles, such as acetonitrile or propionitrile; and sulfoxides, such as dimethyl sulfoxide; and also water; or mixtures of the mentioned solvents; especially suitable are ethers, alcohols, water, carboxylic acids, or mixtures thereof, more especially tetrahydrofuran, pivalic acid or water.

The reactions are advantageously carried out in a temperature range of from about room temperature to the boiling point of the solvent used; preference being given to reaction at 10 to 30° C.

Examples of reducing agents are known to a person skilled in the art, they include hydrides; especially suitable are borohydrides, for example sodium borohydride or sodium cyanoborohydride.

In a preferred embodiment of Variant (A) the reaction is carried out with sodium cyanoborohydride at room temperature, in tetrahydrofuran in the presence of pivalic acid and water.

Especially preferred conditions for this Process variant are described in Examples A1.1, A1.2, A5.1 and A6.1.

Process Variant (B):

Examples of solvents and diluents include those listed above under Process variant (A); especially suitable are esters, water or mixtures thereof, or the use of no solvent.

The reactions are advantageously carried out in a temperature range of from about room temperature to the boiling point of the solvent used; preference being given to reaction at 10 to 30° C.

Examples of a compound $R_E$—C(=O)—$R_Z$ include ketones or aldehydes, for example formaldehyde, acetaldehyde, benzaldehyde or acetone.

In a preferred embodiment of Variant (B) the reaction is carried out with the compound $R_E$—C(=O)—$R_Z$ as the solvent.

In another preferred embodiment of Variant (B) the reaction is carried out with the compound $R_E$—C(=O)—$R_Z$ in a mixture of ethyl acetate and water.

Especially preferred conditions for this Process variant are described, for example, in Examples A7.1 and A7.2.

Process Variant (C):

Examples of solvents and diluents include those listed above under Process variant (A); especially suitable are halogenated hydrocarbons, for example dichloromethane or trichloromethane.

The reactions are advantageously carried out in a temperature range of from 0° C. to the boiling point of the solvent used, preferably from 0° C. to room temperature.

Examples of oxidating agents are known to a person skilled in the art, they include, for example, inorganic salts, for example sodium periodate or potassium permanganate; oxides, for example selenium dioxide or mercury oxide; peroxides, for example hyrogenperoxide or dimethyldioxirane; or peracids; especially suitable are peracids, for example 3-chloroperbenzoic acid or peracetic acid.

Especially preferred conditions for this Process variant are described, for example, in Example A8.1.

Process Variant (D):

Examples of solvents and diluents include those listed above under Process variant (A); especially suitable are alcohols, for example ethanol, methanol or iso-propanol.

Process Variant (D):

Examples of solvents and diluents include those listed above under Process variant (A); especially suitable are alcohols, for example ethanol, methanol or iso-propanol.

The reactions are advantageously carried out in a temperature range of approximately from room temperature to the boiling point of the solvent used.

Examples of a compound $Q_1$-O—$NH_2$ include N-unsubstituted hydroxylamines, for example O-methylhydroxylamine, O-phenylhydroxylamine or hydroxylamine.

In a preferred embodiment of Variant (D) the reaction is carried out with hydroxylamine hydrochloride, in the presence of sodium bicarbonate, at 60° C. in methanol as the solvent.

Especially preferred conditions for this Process variant are described, for example, in Example A4.1.

Process Variant (E):

Examples of solvents and diluents include those listed above under Process variant (A); especially suitable are ethers, alcohols, water, carboxylic acids, or mixtures thereof, more especially tetrahydrofuran, acetic acid or water.

The reactions are advantageously carried out in a temperature range of from about room temperature to the boiling point of the solvent used; preference being given to reaction at 10 to 30° C.

Examples of reducing agents are known to a person skilled in the art, they include hydrides; especially suitable are borohydrides, for example sodium borohydride or sodium cyanoborohydride.

In a preferred embodiment of Variant (E) the reaction is carried out with sodium cyanoborohydride at room temperature, in tetrahydrofuran as the solvent.

Especially preferred conditions for this Process variant are described, for example, in Example A2.1.

Process Variant (F):

Examples of solvents and diluents include those listed above under Process variant (A); especially suitable are ethers, for example diethyl ether or tetrahydrofuran.

The reactions are advantageously carried out in a temperature range of from 0° C. to the boiling point of the solvent used, preferably at room temperature.

Especially preferred conditions for this Process variant are described, for example, in Examples A2.2, A2.3 and A2.6.

Process Variant (G):

Examples of solvents and diluents include those listed above under Process variant (A); especially suitable are ethers, for example diethyl ether or tetrahydrofuran, or aromatic hydrocarbons such as benzene, toluene or xylene, or the use of no solvent.

The reactions are advantageously carried out in a temperature range of from 0° C. to the boiling point of the solvent used, preferably from 0° C. to 80° C.

In a preferred embodiment of Variant (G) the reaction is carried out at 0° C., in tetrahydrofuran as the solvent.

Especially preferred conditions for this Process variant are described, for example, in Example A3.2.

Process Variant (H):

Examples of solvents and diluents include those listed above under Process variant (A); especially suitable are ethers, for example diethyl ether or tetrahydrofuran, or aromatic hydrocarbons such as benzene, toluene or xylene, or the use of no solvent.

The reactions are advantageously carried out in a temperature range of from 0° C. to the boiling point of the solvent used, preferably from 0° C. to 80° C.

In a preferred embodiment of Variant (H) the reaction is carried out at 80° C., in toluene as the solvent.

Especially preferred conditions for this Process variant are described, for example, in Example A3.1.

Process Variant (J):

Examples of solvents and diluents include those listed above under Process variant (A); especially suitable are hydrocarbons, aromatic hydrocarbons, halogenated hydrocarbons, esters or ethers, for example hexane, toluene, dichloromethane, ethyl acetate or tetrahydrofuran; or water; or mixtures thereof.

The reactions are advantageously carried out in a temperature range of from 0° C. to the boiling point of the solvent used, preferably from 0° C. to room temperature; in the presence of a base, for example an inorganic base, such as sodium hydroxide, potassium hydroxide, sodium carbonate or sodium bicarbonate, or an organic base, such as pyridine, triethylamine or N-ethyl-N,N-diisopropylamine; or without the presence of a base.

In a preferred embodiment of Variant (J) the reaction is carried out in the presence of bicarbonate at room temperature, in a mixture of ethyl acetate and water as the solvent.

In another preferred embodiment of Variant (J) the reaction is carried out without a base at room temperature, in ethyl acetate as the solvent.

Especially preferred conditions for this Process variant are described, for example, in Examples A1.3, A1.4 and A2.4.

Process Variant (K):

Examples of solvents and diluents include those listed above under Process variant (A); especially suitable are hydrocarbons, aromatic hydrocarbons, halogenated hydrocarbons, esters or ethers, for example hexane, toluene, dichloromethane, ethyl acetate or tetrahydrofuran; or water; or mixtures thereof.

The reactions are advantageously carried out in a temperature range of from 0° C. to the boiling point of the solvent used, preferably from 0° C. to room temperature; in the presence of a base, for example an inorganic base, such as sodium hydroxide, potassium hydroxide, sodium carbonate or sodium bicarbonate, or an organic base, such as pyridine, triethylamine or N-ethyl-N,N-diisopropylamine; or without the presence of a base.

In a preferred embodiment of Variant (K) the reaction is carried out in the presence of bicarbonate at room temperature, in a mixture of ethyl acetate and water as the solvent.

In another preferred embodiment of Variant (K) the reaction is carried out without a base at room temperature, in ethyl acetate as the solvent.

Especially preferred conditions for this Process variant are described, for example, in Examples A2.7 and A2.8.

Process Variant (L):

Examples of solvents and diluents include those listed above under Process variant (A); especially suitable are ethers, for example diethyl ether or tetrahydrofuran, or aromatic hydrocarbons such as benzene, toluene or xylene, or the use of no solvent.

The reactions are advantageously carried out in a temperature range of from 0° C. to the boiling point of the solvent used, preferably from 0° C. to 80° C.

In a preferred embodiment of Variant (L) the reaction is carried out at room temperature, without the use of a solvent.

Especially preferred conditions for this Process variant are described, for example, in Example A2.5.

The compounds of formula (I) may be in the form of one of the possible isomers or in the form of a mixture thereof, in the form of pure isomers or in the form of an isomeric mixture, i.e. in the form of a diastereomeric mixture; the invention relates both to the pure isomers and to the diastereomeric mixtures and is to be interpreted accordingly hereinabove and hereinbelow, even if stereochemical details are not mentioned specifically in every case.

The diastereomeric mixtures can be resolved into the pure isomers by known methods, for example by recrystallisation from a solvent, by chromatography, for example high pressure liquid chromatography (HPLC) on acetylcellulose, with the aid of suitable micro-organisms, by cleavage with specific, immobilised enzymes, or via the formation of inclusion compounds, for example using crown ethers, only one isomer being complexed.

Apart from by separation of corresponding mixtures of isomers, pure diastereoisomers can be obtained according to the invention also by generally known methods of stereoselective synthesis, for example by carrying out the process according to the invention using starting materials having correspondingly suitable stereochemistry.

In each case it is advantageous to isolate or synthesise the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and all or some of the remaining steps are carried out, or in which a starting material is used in the form of a derivative and/or a salt and/or its diastereomers, or, especially, is formed under the reaction conditions. For instance compounds of formula (I) bearing a functional group or a protecting group, preferably in the 5-position, can be used as starting materials for the preparation of further compounds of formula (I). For such manipulations methods known to the person skilled in the art can be applied.

In the processes of the present invention it is preferable to use those starting materials and intermediates which result in the compounds of formula (I) that are especially preferred.

The invention relates especially to the preparation processes described in Examples A1.1 to A8.1.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects, preferably of the orders *Lepidoptera*; Coleoptera, *Homoptera*, Orthoptera, *Isoptera*, Psocoptera, Anoplura, Mallophaga, Thysanoptera; Heteroptera, *Siphonaptera*, Hymentoptera and Thysanura, and representatives of the order Acarina, nematodes, cestodes and trematodes, while at the same time protecting useful organisms. The said animal pests especially include, for example, those mentioned in European Patent Application EP-A-736 252, page 5, line 55, to page 6, line 55. The pests mentioned therein are therefore included by reference in the subject matter of the present invention.

The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii*, *Heterodora avenae* and *Heterodora trifolii; Globodera* spp., e.g. *Globodera rostochiensis; Meloidogyne* spp., e.g. *Meloidogyne incognita* and *Meloidogyne javanica; Radopholus* spp., e.g. *Radopholus simiis; Pratylenchus*, e.g. *Pratylenchus neglectans* and *Pratylenchus penetrans; Tylenchulus*, e.g. *Tylenchulus semipenetrans; Longidorus, Trichodorus, Xiphinema, Ditylenchus, Apheenchoides* and *Anguina; insbesondere Meloidogyne*, e.g. *Meloidogyne incognita*, and *Heterodera*, e.g. *Heterodera glycines*.

An especially important aspect of the present invention is the use of the compounds of formula (I) according to the invention in the protection of plants against parasitic feeding pests.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from attack by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

As formulation adjuvants there are used, for example, solid carriers, solvents, stabilisers, "slow release" adjuvants, colouringsi and optionally surface-active substances (surfactants). Suitable carriers and adjuvants include all substances customarily used. As adjuvants, such as solvents, solid carriers, surface-active compounds, non-ionic surfactants, cationic surfactants, anionic surfactants and further adjuvants in the compositions used according to the invention, there come into consideration, for example, those described in EP-A-736 252, page 7, line 51 to page 8, line 39.

The compositions for use in crop protection and in humans, domestic animals and productive livestock generally comprise from 0.1 to 99%, especially from 0.1 to 95%, of active ingredient and from 1 to 99.9%, especially from 5 to 99.9%, of at least one solid or liquid adjuvant, the composition generally including from 0 to 25%, especially from 0.1 to 20%, of surfactants (% is percent by weight in each case). Whereas commercial products will preferably be formulated as concentrates, the end user will normally employ dilute formulations having considerably lower concentrations of active ingredient.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from strain NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; clothianidin; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; pyridalyl; fenazaquin; pyriproxyfen; pyrimidifen; nitenpyram; acetamiprid; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; flonicamid; iprobenfos; isofenphos; isoxathion; ivermectin; malathion; mecarbam; mesulfenphos; metaldehyde; metolcarb; milbemectin; moxidectin; naled; NC 184; nithiazine; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiamethoxam; thiodicarb; thiofanox; thionazin; thuringiensin; tralomethrin; triarathene; triazophos; triazuron; trichlorfon; triflumuron; trimethacarb; vamidothion; xylylcarb; etoxazole; zetamethrin; indoxacarb; methoxyfenozide; bifenazate; XMC (3,5-xylyl methylcarbamate); or the fungus pathogen *Metarhizium anisopliae*.

Preferred crop protection products have especially the following compositions (% is percent by weight):

Emulsifiable Concentrates:

active ingredient: 1 to 90%, preferably 5 to 20% surfactant: 1 to 30%, preferably 10 to 20% solvent: 5 to 98%, preferably 70 to 85%

Dusts:

active ingredient: 0.1 to 10%, preferably 0.1 to 1% solid carrier: 99.9 to 90%, preferably 99.9 to 99%

Suspension Concentrates:

active ingredient: 5 to 75%, preferably 10 to 50% water: 94 to 24%, preferably 88 to 30% surfactant: 1 to 40%, preferably 2 to 30%

Wettable Powders:

active ingredient: 0.5 to 90%, preferably 1 to 80% surfactant: 0.5 to 20%, preferably 1 to 15% solid carrier: 5 to 99%, preferably 15 to 98%

Granules:

active ingredient: 0.5 to 30%, preferably 3 to 15% solid carrier: 99.5 to 70%, preferably 97 to 85%

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil; preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant(s). The invention relates likewise to those processes for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha, more especially from 20 to 600 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, including propagation material of genetically modified plants, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

PREPARATION EXAMPLES

Example A1.1

4"-Desoxy-4"-(R)—(N-hydroxy-amino)-avermectin B1

11.9 g of 4"-desoxy-4"-(N-hydroxy-imino)-avermectin B1 are dissolved in 36 ml of tetrahydrofuran. 4.5 ml pivalic acid and 0.5 ml of water are added, followed by 2.1 g sodium cyanoborohydride. The mixture is stirred at room temperature for 14 hours at room temperature. Then 30 ml saturated aqueous sodium bicarbonate are added and the mixture is extracted with ethyl acetate. The phases are then separated; the organic phase is dried over sodium sulfate and the solvents are distilled off. The residue is purified by chromatography on silica gel with hexane/ethyl acetate, yielding 4"-desoxy-4"-(R)—(N-hydroxy-amino)-avermectin B1.

Example A1.2

4"-Desoxy-4"-(R)—(N-methoxy-amino)-avermectin B1

8 g of 4"-desoxy-4"-(N-methoxy-imino)-avermectin B1 are dissolved in 20 ml of tetrahydrofuran. 1.9 ml pivalic acid and 0.4 ml of water are added, followed by 0.73 g sodium cyanoborohydride. The mixture is stirred at room temperature for 14 hours at room temperature. Then 20 ml saturated aqueous sodium bicarbonate are added and the mixture is extracted with ethyl acetate. The phases are then separated; the organic phase is dried over sodium sulfate and the solvents are distilled off. The residue is purified by chromatography on silica gel with hexane/ethyl acetate, yielding 4"-desoxy-4"-(R)—(N-methoxy-amino)-avermectin B1.

Example A1.3

4"-Desoxy-4"-(R)—(N-methoxycarbonyloxy-amino)-avermectin B1

4.4 g 4"-desoxy-4"-(R)—(N-hydroxy-amino)-avermectin B1 (Example A1.1) are dissolved in a mixture of 30 ml ethyl acetate and 30 ml saturated aqueous sodium bicarbonate. 0.47 g methyl chloroformate are added and the mixture is vigorously stirred for 14 hours at room temperature. The phases are then separated; the organic phase is dried over sodium sulfate and the solvents are distilled off. The residue is purified by chromatography on silica gel with hexane/ethyl acetate, yielding 4'-desoxy-4'-(R)—(N-methoxycarbonyloxy-amino)-avermectin B1 (Example A1.3) and 4"-desoxy-4"-(R)—(N-hydroxy-N-methoxycarbonyl-amino)-avermectin B1 (Example A2.7).

Example A1.4

4"-Desoxy-4"-(R)—(N-phenylaminocarbonyloxy-amino)-avermectin B1

4.4 g 4"-desoxy-4"-(R)—(N-hydroxy-amino)-avermectin B1 (Example A1.1) are dissolved in 30 ml ethyl acetate. 0.72 g phenylisocyanate are added and the mixture is stirred for 3 hours at room temperature. Then the solvent is distilled off, and the residue is purified by chromatography on silica gel with hexane/ethyl acetate, yielding 4"-desoxy-4"-(R)—(N-phenyl-aminocarbonyloxy-amino)-avermectin B1 (Example A1.4) and 4"-desoxy-4"-(R)—(N-hydroxy-N-phenylaminocarbonyl-amino)-avermectin B1 (Example A2.8).

Example A2.1

4"-Desoxy-4"-(R)—(N-hydroxy-N-methyl-amino)-avermectin B1

3.6 g 4"-desoxy-4"-(R)—(N-methylene-amino)-avermectin-N-oxide B1 (Example A7.1) are dissolved in 40 ml tetrahydrofuran. 0.28 g sodium cyanoborohydride are added, and the mixture is stirred for 4 hours at room temperature. Then the mixture is extracted with aqueous sodium bicarbonate (1 mol/l) and ethyl acetate. The phases are separated; the organic phase is dried over sodium sulfate and the solvents are distilled off. The residue is purified by chromatography on silica gel with hexane/ethyl acetate, yielding 4"-desoxy-4"-(R)—(N-hydroxy-N-methyl-amino)-avermectin B1.

Example A2.2

4"-Desoxy-4"-(R)—(N-hydroxy-N-ethyl-amino)-avermectin B1

4.5 g 4"-desoxy-4"-(R)—(N-methylene-amino)-avermectin-N-oxide B1 (Example A7.1) are dissolved in 80 ml tetrahydrofuran. 6.7 ml methylmagnesium bromide (3 mol/l solution in diethylether) are added, and the mixture is stirred for 1 hour at room temperature. Then the mixture is extracted with saturated aqueous ammonium chloride and ethyl acetate. The phases are separated; the organic phase is dried over sodium sulfate and the solvents are distilled off. The residue is purified by chromatography on silica gel with hexane/ethyl acetate, yielding 4"-desoxy-4"-(R)—(N-hydroxy-N-ethyl-amino)-avermectin B1.

Example A2.3

4"-Desoxy-4"-(R)—(N-hydroxy-N-isopropyl-amino)-avermectin B1

4.3 g 4"-desoxy-4"-(R)—(N-ethylidene-amino)-avermectin-N-oxide B1 (Example A7.2) are dissolved in 50 ml tetrahydrofuran. 5 ml methylmagnesium bromide (3 mol/l solution in diethylether) are added, and the mixture is stirred for 1 hour at room temperature. Then the mixture is extracted with saturated aqueous ammonium chloride and ethyl acetate. The phases are separated; the organic phase is dried over sodium sulfate and the solvents are distilled off. The residue is purified by chromatography on silica gel with hexane/ethyl acetate, yielding 4"-desoxy-4"-(R)—(N-hydroxy-N-isopropyl-amino)-avermectin B1.

Example A2.4

4"-Desoxy-4"-(R)—(N-hydroxy-N-benzyl-amino)-avermectin B1

2.7 g of 4"-desoxy-4"-(R)—(N-hydroxy-amino)-avermectin B1 (Example A1.1) are dissolved in a mixture of 30 ml ethyl acetate and 30 ml saturated aqueous sodium bicarbonate. Then 5.2 g benzyl bromide are added, and the mixture is stirred for 48 hours at 60° C. After cooling to room temperature, the phases are separated; the organic phase is dried over sodium sulfate and the solvents are distilled off. The residue is purified by chromatography on silica gel with hexane/ethyl acetate, yielding 4"-desoxy-4"-(R)—(N-hydroxy-N-benzyl-amino)-avermectin B1.

Example A2.5

4"-Desoxy-4"-(R)-[N-hydroxy-N-(2-ethoxycarbonyl-ethyl)-amino]-avermectin B1

4.5 g of 4"-desoxy-4"-(R)—(N-hydroxy-amino)-avermectin B1 (Example A1.1) are dissolved in 10 ml of ethyl acrylate. The mixture is stirred at room temperature for 18 hours, then the solvent is distilled off. The residue is purified by chromatography on silica gel with hexane/ethyl acetate, yielding 4"-desoxy-4"-(R)-[N-hydroxy-N-(2-ethoxycarbonyl-ethyl)-amino]-avermectin B1.

Example A2.6

4"-Desoxy-4"-(R)-[N-hydroxy-N-(4-hydroxy-4-methyl-pent-2-yn-1-yl)-amino]-avermectin B1

Under an atmosphere of nitrogen, 0.46 g 2-methyl-3-butyne-2-ol and 1.4 g N-ethyl-N,N-diisopropylamine are dissolved in 100 ml dichloromethane. Then 1.8 g zinc trifluoromethanesulfonate are added, and the mixture is stirred for 3 hours at room temperature. Then a solution of 4.5 g 4"-desoxy-4"-(R)—(N-methylene-amino)-avermectin-N-oxide B1 (Example A7.1) in 100 ml toluene are added. Subsequently, most of the dichloromethane is distilled off, and the remaining solution is stirred at 70° C. for 14 hours. Then the mixture is cooled to room temperature, extracted with saturated aqueous sodium bicarbonate and ethyl acetate, the phases are separated, the organic phase is dried over sodium sulfate and the solvent is distilled off. The residue is purified by chromatography on silica gel with hexane/ethyl acetate, yielding 4"-Desoxy-4"-(R)-[N-hydroxy-N-(4-hydroxy-4-methyl-pent-2-yn-1-yl)-amino]-avermectin B1.

Example A2.7

4"-desoxy-4"-(R)—(N-hydroxy-N-methoxycarbonyl-amino)-avermectin B1

The compound is obtained by the same procedure as described in Example A1.3.

Example A2.8

4"-desoxy-4"-(R)—(N-hydroxy-N-phenylaminocarbonyl-amino)-avermectin B1

The compound is obtained by the same procedure as described in Example A1.4.

Example A3.1

4"-Desoxy-4"-(R)-(5-hydroxymethyl-isoxazolidin-2-yl)-avermectin B1

4.5 g 4"-desoxy-4"-(R)—(N-methylene-amino)-avermectin-N-oxide B1 (Example A7.1) and 4.4 ml prop-2-en-1-ol are dissolved in 150 ml of toluene. The mixture is stirred for 14 hours at 80° C. Then the solvent is distilled off. The residue is purified by chromatography on silica gel with hexane/ethyl acetate, yielding 4"-desoxy-4"-(R)-(5-hydroxymethyl-isoxazolidin-2-yl)-avermectin B1.

Example A3.2

4"-Desoxy-4"-(R)-(4,5-bis-ethoxycarbonyl-3H-isoxazol-2-yl)-avermectin B1

4.5 g 4"-desoxy-4"-(R)—(N-methylene-amino)-avermectin-N-oxide B1 (Example A7.1) is dissolved in 60 ml of tetrahydrofuran. The mixture is cooled to 0° C., then 0.9 ml but-2-yne-dioic acid diethyl ester are added, and the mixture is stirred at 0° C. for 3 hours. Then the solvent is distilled off and the residue is purified by chromatography on silica gel with hexane/ethyl acetate, yielding 4"-desoxy-4"-(R)-(4,5-bis-ethoxycarbonyl-3H-isoxazol-2-yl)-avermectin B1.

Example A4.1

4"-Desoxy-4"-(S)—(N-hydroxy-amino)-avermectin B1

7.7 g 4"-desoxy-4"-(S)—(N-cyanomethylene-amino)-avermectin-N-oxide B1 (Example A8.1) are dissolved in 50 ml methanol, 2.8 g hydroxylamine hydrochloride and 3.6 g sodium bicarbonate are added, and the mixture is stirred at 60° C. for 3 hours. After cooling to room temperature, the solvent is distilled off, and the residue is extracted with aqueous sodium bicarbonate (1 mol/l) and ethyl acetate. Then the phases are separated; the organic phase is dried over sodium sulfate and the solvent is distilled off. The residue is purified by chromatography on silica gel with hexane/ethyl acetate, yielding 4"-desoxy-4"-(S)—(N-hydroxy-amino)-avermectin B1.

Example A5.1

4"-Desoxy-4"-(R)—(N-hydroxy-amino)-22,23-dihydro-avermectin B1

4.8 g of 4"-desoxy-4"-(N-hydroxy-imino)-22,23-dihydro-avermectin B1 are dissolved in 15 ml of tetrahydrofuran. 1.8 ml pivalic acid and 0.2 ml of water are added, followed by 0.9 g sodium cyanoborohydride. The mixture is stirred at room temperature for 14 hours at room temperature. Then 15 ml saturated aqueous sodium bicarbonate are added and the mixture is extracted with ethyl acetate. The phases are then separated; the organic phase is dried over sodium sulfate and the solvents are distilled off. The residue is purified by chromatography on silica gel with hexane/ethyl acetate, yielding 4"-desoxy-4"-(R)—(N-hydroxy-amino)-22,23-dihydro-avermectin B1.

Example A6.1

4'-Desoxy-4'-(R)—(N-hydroxy-amino)-avermectin monosaccharide B1

10 g of 4'-desoxy-4'-(N-hydroxy-imino)-avermectin monosaccharide B1 are dissolved in 40 ml of tetrahydrofuran. 4.5 ml pivalic acid and 0.5 ml of water are added, followed by 2.6 g sodium cyanoborohydride. The mixture is stirred at room temperature for 14 hours at room temperature. Then 40 ml saturated aqueous sodium bicarbonate are added and the mixture is extracted with ethyl acetate. The phases are then separated; the organic phase is dried over sodium sulfate and the solvents are distilled off. The residue is purified by chromatography on silica gel with hexane/ethyl acetate, yielding 4'-desoxy-4'-(R)—(N-hydroxy-amino)-avermectin monosaccharide B1.

Example A7.1

4"-Desoxy-4"-(R)—(N-methylene-amino)-avermectin-N-oxide B1

8.9 g 4"-desoxy-4"-(R)—(N-hydroxy-amino)-avermectin B1 (Example A1.1) are dissolved in 50 ml ethyl acetate, 70 ml aqueous formaldehyde are added, and the mixture is stirred vigorously for 3 hours at room temperature. The phases are then separated; the organic phase is dried over sodium sulfate and the solvents are distilled off. The residue is purified by chromatography on silica gel with hexane/ethyl acetate, yielding 4"-desoxy-4"-(R)—(N-methylene-amino)-avermectin-N-oxide B1.

Example A7.2

4"-Desoxy-4"-(R)—(N-ethylidene-amino)-avermectin-N-oxide B1

8.9 g 4"-desoxy-4"-(R)—(N-hydroxy-amino)-avermectin B1 (Example A1.1) are dissolved in 50 ml acetaldehyde, and the mixture is stirred for 30 minutes at room temperature. Then the solvent is distilled off. The residue is purified by chromatography on silica gel with hexane/ethyl acetate, yielding 4"-desoxy-4"-(R)—(N-ethylidene-amino)-avermectin-N-oxide B1.

Example A8.1

4"-Desoxy-4"-(S)—(N-cyanomethylene-amino)-avermectin-N-oxide B1

3 g 4"-desoxy-4"-(S)—(N-cyanomethyl-amino)-avermectin B1 are dissolved in 20 ml dichloromethane, 1.6 g 3-chloroperbenzoic acid are added and the mixture is stirred for 30 minutes at room temperature. Then 20 ml aqueous sodium bicarbonate (1 mol/l) are added, and after extraction the phases are separated; the organic phase is dried over sodium sulfate and the solvent is distilled off. The residue is purified by chromatography on silica gel with hexane/ethyl acetate, yielding 4"-desoxy-4"-(S)—(N-cyanomethylene-amino)-avermectin-N-oxide B1.

Similarly to the preparation examples above it is also possible to prepare the compounds listed in Tables A1 to A8 and Tables 1 to 48. In the Tables, the symbol ⁓⁓⁓ denotes the bond through which the radical in question is attached to the N-, O- or C-atom of the skeleton.

Since in most cases the compounds are present as mixtures of the avermectin derivatives B1a and B1b, characterization by customary physical data such as melting point or refractive index makes little sense. For this reason, the compounds are characterized by the retention times which are determined in an analysis by HPLC (high performance liquid chromatography). Here, the term B1a refers to the main component in which $R_1$ is sec-butyl, with a content of usually more than 80%. B1b denotes the minor component in which $R_1$ is isopropyl. Where two retention times are given both for the B1a and for the B1b derivative or both, the compounds are mixtures of diastereomers which can be separated chromatographically. In the case of compounds where a retention time is given only in column B1a or only in column B1b, the pure B1a or B1b component, respectively, can be obtained during work-up. The correct structures of the B1a and B1b components are assigned by mass spectrometry.

The following method is used for HPLC analysis:

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [μl/min] |
| 0 | 80 | 20 | 500 |
| 0.1 | 50 | 50 | 500 |
| 10 | 5 | 95 | 500 |
| 15 | 0 | 100 | 500 |
| 17 | 0 | 100 | 500 |
| 17.1 | 80 | 20 | 500 |
| 22 | 80 | 20 | 500 |
| Type of column | | YMC-Pack ODS-AQ | |
| Column length | | 125 mm | |
| Internal diameter of column: | | 2 mm | |
| Temperature | | 40° C. | |

The YMC-Pack ODS-AQ column used for the chromatography of the compounds is manufactured by YMC, Alte Raesfelderstrasse 6, 46514 Schermbeck, Germany.

TABLE A1

Compounds of the formula (I) in which $R_1$ is sec-butyl or isopropyl

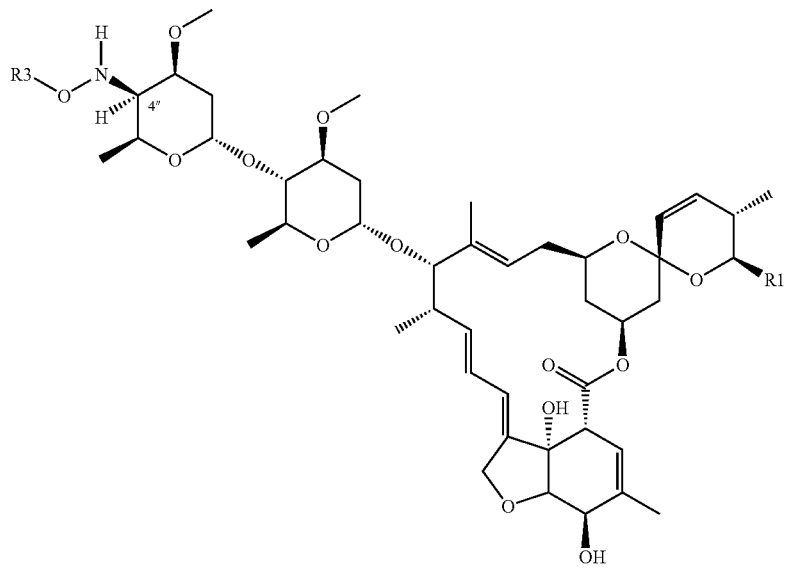

| | | Retention time (min) | |
|---|---|---|---|
| No. | $R_3$ | B1a | B1b |
| A1.1 | H | 5.10 | 4.76 |
| A1.2 | methyl | 9.16 | 8.44 |
| A1.3 | ―C(=O)OCH3 | 9.54 | 8.86 |
| A1.4 | ―C(=O)NHC6H5 | 11.18 | |
| A1.5 | ethyl | 9.50 | 8.85 |
| A1.6 | $CH_2=CH-CH_2-$ | 10.41 | 9.73 |
| A1.7 | ―C(=O)CH2OCH3 | 9.18 | 8.58 |
| A1.8 | CH3OCH2CH2OCH2― | 5.39 | |

TABLE A1-continued
Compounds of the formula (I) in which $R_1$ is sec-butyl or isopropyl
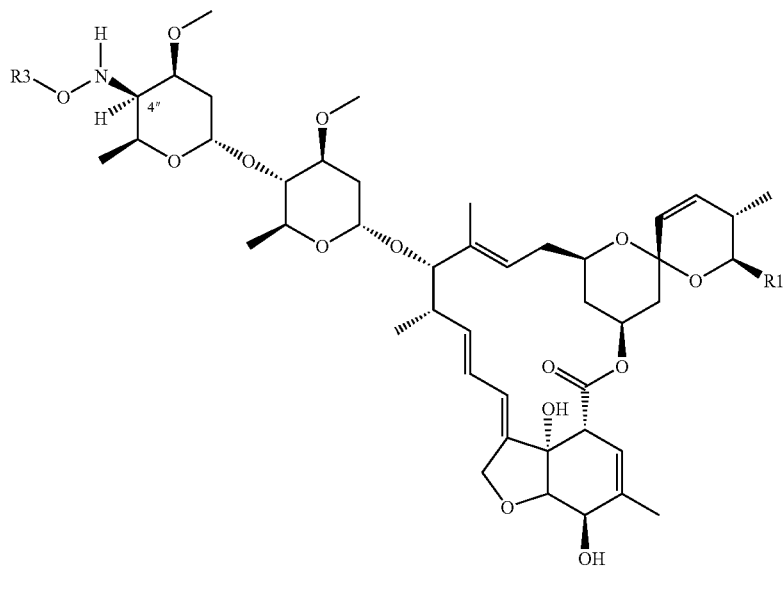
| No. | $R_3$ | Retention time (min) B1a | B1b |
|---|---|---|---|
| A1.9 | $H_2N-\overset{O}{\underset{\|\|}{C}}-$ | 8.16 | 7.47 |
TABLE A2
Compounds of the formula (I) in which $R_1$ is sec-butyl or isopropyl
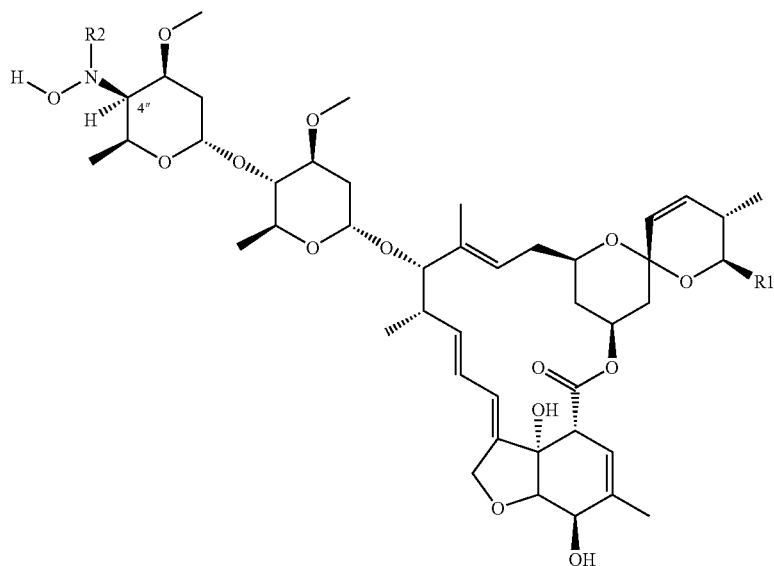
| No. | $R_3$ | Retention time (min) B1a | B1b |
|---|---|---|---|
| A2.1 | methyl | 6.59 | 6.19 |
| A2.2 | ethyl | 5.65 | 5.18 |
| A2.3 | iso-propyl | 5.66 | 5.01 |

TABLE A2-continued
Compounds of the formula (I) in which $R_1$ is sec-butyl or isopropyl
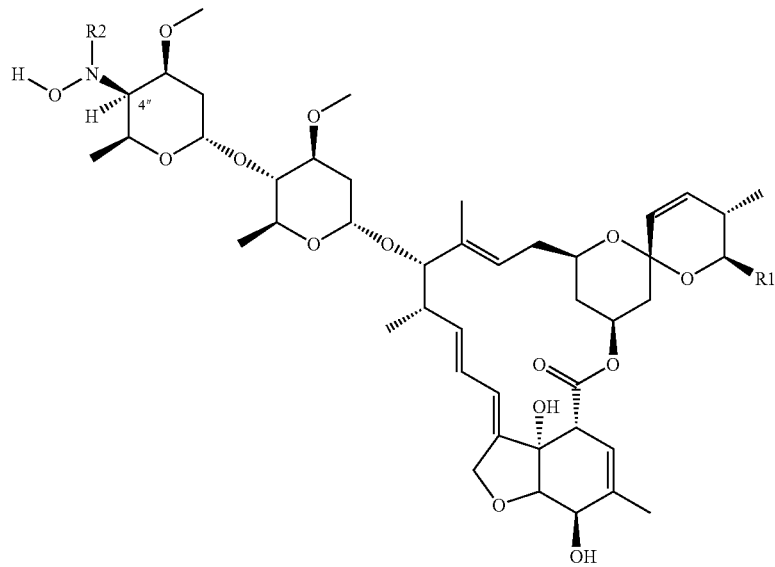
|     |     | Retention time (min) | |
| --- | --- | --- | --- |
| No. | $R_3$ | B1a | B1b |
| A2.4 | (benzyl) | 9.55 | 9.12 |
| A2.5 | (ethyl propanoate) | 10.14 | 9.50 |
| A2.6 | (2-methyl-3-butyn-2-ol) | 7.10 | 6.52 |
| A2.7 | (methyl carbonate) | 7.90 | 7.28 |
| A2.8 | (phenylcarbamoyl) | 9.50 | |
| A2.9 | $CH_2=CH-CH_2-$ | 6.38 | 5.89 |
| A2.10 | n-propyl | 6.03 | 5.55 |
| A2.11 | n-butyl | 6.44 | 5.92 |

TABLE A2-continued
Compounds of the formula (I) in which $R_1$ is sec-butyl or isopropyl
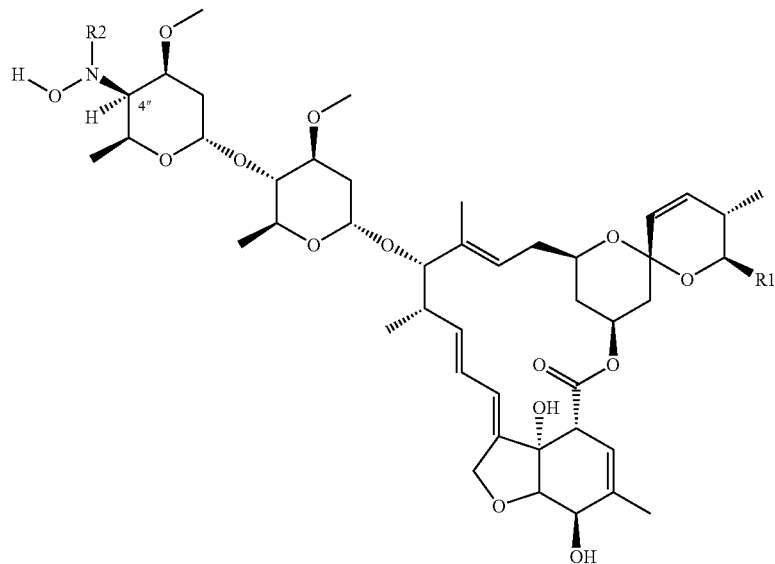
|  |  | Retention time (min) | |
| --- | --- | --- | --- |
| No. | $R_3$ | B1a | B1b |
| A2.12 | ethyl ester group | 9.35 | 8.73 |
| A2.13 | acetyl group | 9.30 | 8.75 |
| A2.14 | methoxyacetyl group | 9.09 | |

TABLE A2-continued
Compounds of the formula (I) in which $R_1$ is sec-butyl or isopropyl
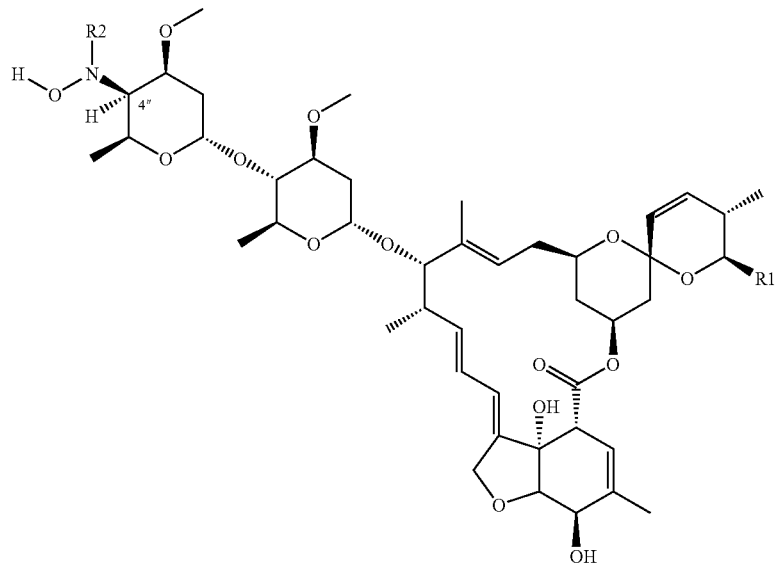
|  |  | Retention time (min) | |
|---|---|---|---|
| No. | $R_3$ | B1a | B1b |
| A2.15 |  | 8.66 | 8.01 |
| A2.16 | CH≡C—CH$_2$—<br>n-pentyl | 7.02 | 6.45 |
| A2.17 | H—C(=O)— | 10.35 | 9.55 |
| A2.18 | H$_2$—C(=O)— | 6.88 |  |

TABLE A3
Compounds of the formula (I) in which R₁ is sec-butyl B1a) or isopropyl
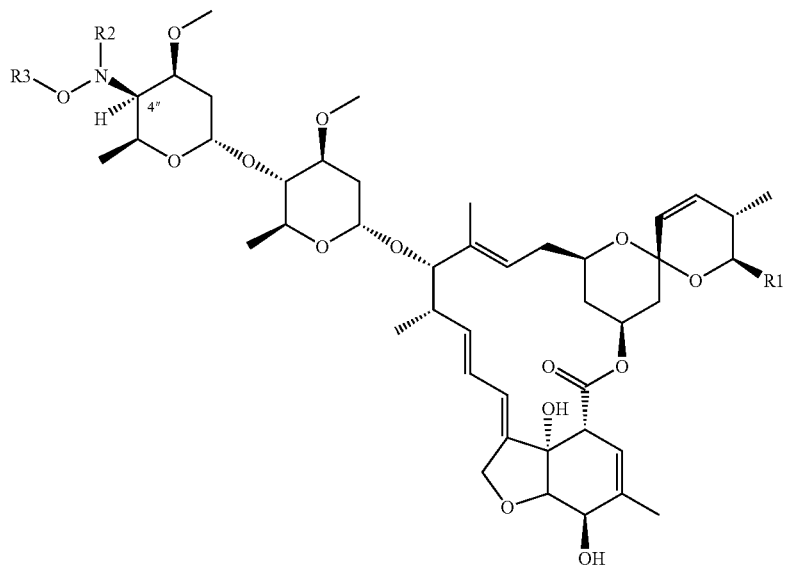
| No. | 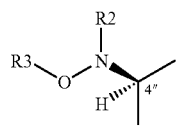 | Retention time (min) B1a | B1b |
|---|---|---|---|
| A3.1 | 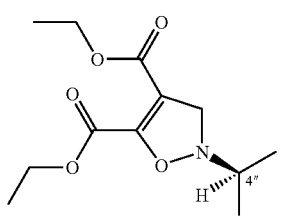 | 5.53/5.42 | 5.12/5.07 |
| A3.2 | | 11.07 | |
| A3.3 | 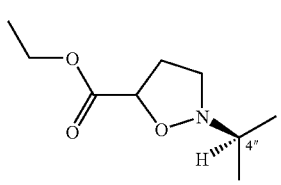 | 9.47/8.87 | |

TABLE A3-continued
Compounds of the formula (I) in which $R_1$ is sec-butyl B1a) or isopropyl
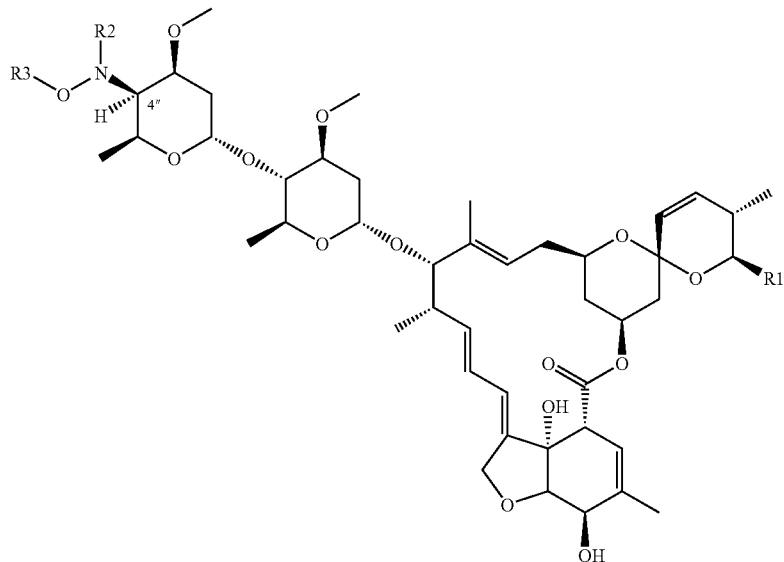
| No. | 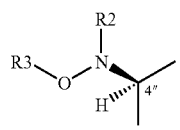 | Retention time (min) B1a   B1b |
|-----|---|---|
| A3.4 | 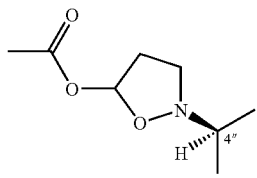 | 9.40/9.10 |
| A3.5 | 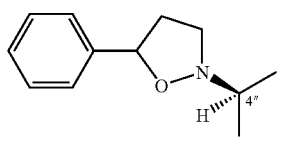 | 8.48/8.27 |

TABLE A4
Compounds of the formula (I) in which and $R_1$ is sec-butyl or isopropyl
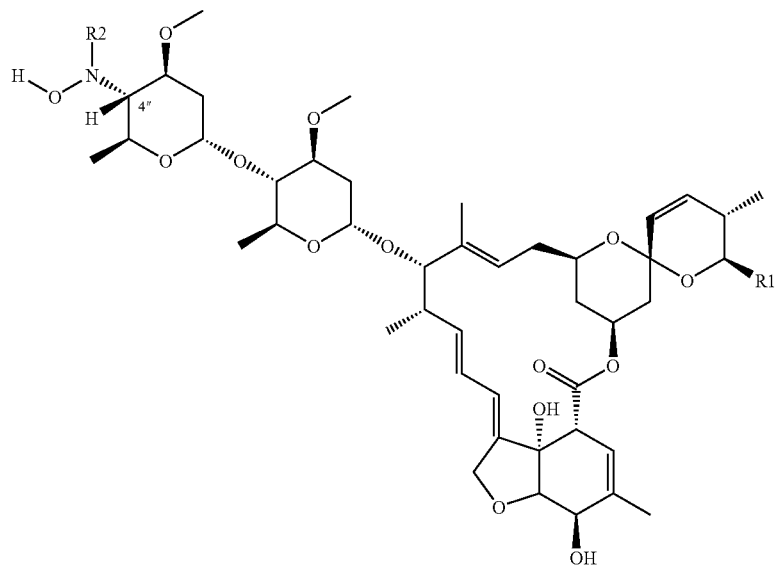
| No. | $R_2$ | $R_3$ | Retention time (min) B1a | B1b |
|---|---|---|---|---|
| A4.1 | H | H | 5.23 | |
| A4.2 | H | $CH_3OCH_2CH_2OCH_2$— | 5.68 | |
TABLE A5
Compounds of the formula (I) in which A is A1, n is 1, X—Y is —$CH_2$—$CH_2$— and $R_1$ is sec-butyl (B1a) or isopropyl (B1b).
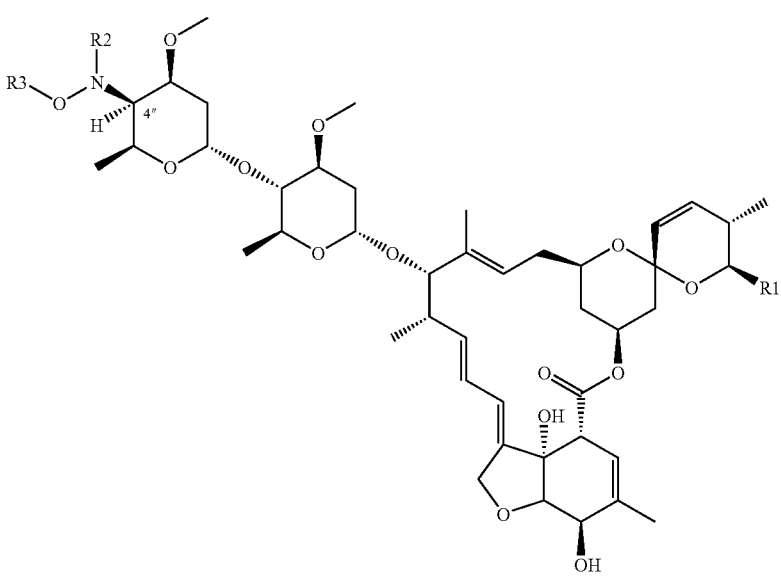
| No. | $R_2$ | $R_3$ | Retention time (min) B1a | B1b |
|---|---|---|---|---|
| A5.1 | H | H | 6.93 | 6.45 |
| A5.2 | H-C(=O)- | H | 12.12 | 11.47 |

TABLE A6

Compounds of the formula (I) in which $R_1$ is sec-butyl or isopropyl

|  |  | Retention time (min) | |
| --- | --- | --- | --- |
| No. | $R_2$ | $R_3$ | B1a | B1b |
| A6.1 | H | H | 4.96 | |
| A6.2 | H | H | 6.93 | 6.45 |
| A6.3 | H-C(=O)- | H | 12.12 | 11.47 |

TABLE A7

Compounds of the formula (I) in which $R_1$ is sec-butyl B1a) or isopropyl

|  |  |  | Retention time (min) | |
| --- | --- | --- | --- | --- |
| No. | $R_Z$ | $R_E$ | B1a | B1b |
| A7.1 | H | H | | |
| A7.2 | methyl | H | 7.31 | 6.62 |
| A7.3 | ethyl | H | 8.16 | |
| A7.4 | iso-propyl | H | 8.70 | 8.05 |
| A7.5 | phenyl | H | 11.58 | 10.78 |
| A7.6 | CN | H | 9.45 | 9.05 |

TABLE A7-continued
Compounds of the formula (I) in which R₁ is sec-butyl B1a) or isopropyl
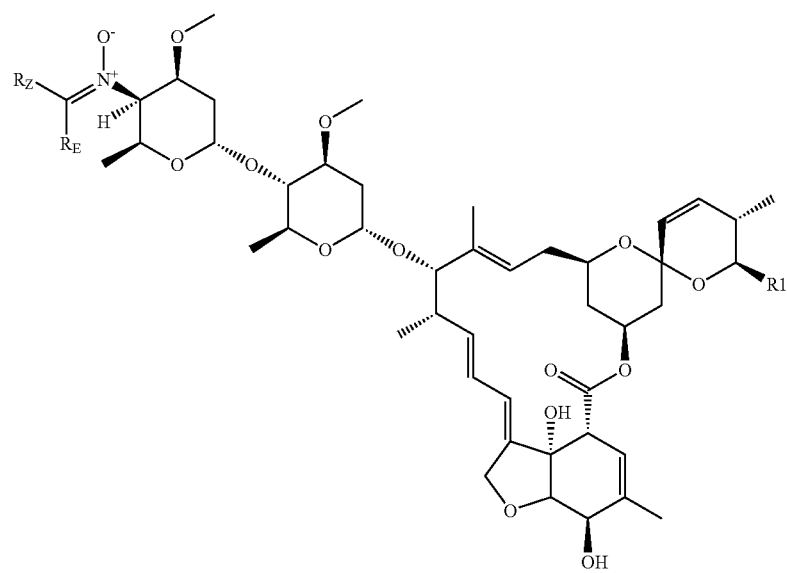
|  |  |  | Retention time (min) | |
|---|---|---|---|---|
| No. | $R_Z$ | $R_E$ | B1a | B1b |
| A7.7 | n-butyl | H | 9.12 | 8.37 |
| A7.8 | (2-allyloxyphenyl) | H | 10.47 | 9.81 |
TABLE A8
Compounds of the formula (I) in which R₁ is sec-butyl or isopropyl
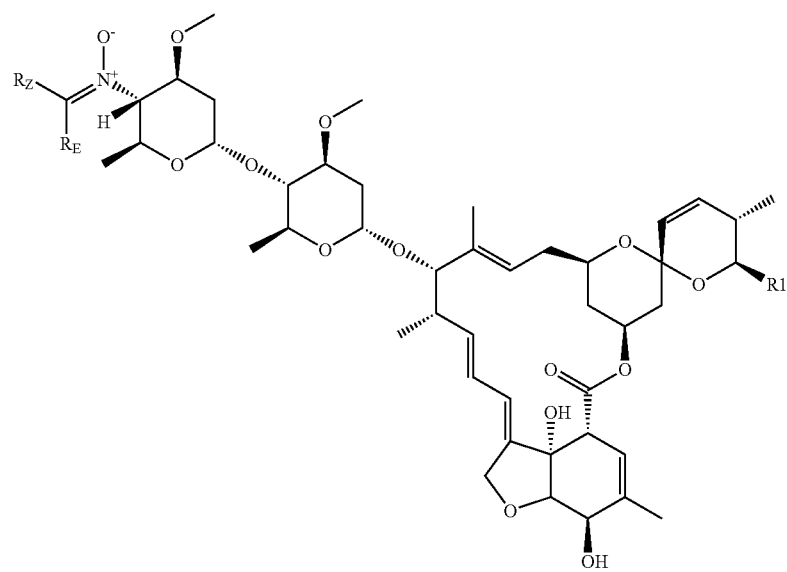
|  |  |  | Retention time (min) | |
|---|---|---|---|---|
| No. | $R_Z$ | $R_E$ | B1a | B1b |
| A8.1 | CN | H | 10.01 | |

TABLE B

Compounds of the formula (I) and (II) wherein U is —N(R$_2$)OR$_3$ and R$_2$ and R$_3$ have the following meanings:

| No. | R$_2$ | R$_3$ |
|---|---|---|
| B1.1 | methyl | H |
| B1.2 | ethyl | H |
| B1.3 | n-propyl | H |
| B1.4 | iso-propyl | H |
| B1.5 | n-butyl | H |
| B1.6 | s-butyl | H |
| B1.7 | iso-butyl | H |
| B1.8 | t-butyl | H |
| B1.9 | CH$_2$=CH—CH$_2$— | H |
| B1.10 | CH$_3$—CH=CH—CH$_2$— | H |
| B1.11 | HO—CH$_2$—CH$_2$— | H |
| B1.12 | phenyl | H |
| B1.13 | benzyl | H |
| B1.14 | (phenethyl) | H |
| B1.15 | (ethoxycarbonylmethyl) | H |
| B1.16 | (ethoxycarbonylethyl) | H |
| B1.17 | (formyl) | H |
| B1.18 | (acetyl) | H |
| B1.19 | (propionyl) | H |
| B1.20 | (acryloyl) | H |
| B1.21 | (butyryl) | H |
| B1.22 | (crotonoyl) | H |
| B1.23 | (isobutyryl) | H |
| B1.24 | (methoxyacetyl) | H |
| B1.25 | (ethoxyacetyl) | H |
| B1.26 | (2-hydroxyethoxyacetyl) | H |
| B1.27 | benzoyl | H |
| B1.28 | (methoxycarbonyl) | H |
| B1.29 | (ethoxycarbonyl) | H |
| B1.30 | (carbamoyl) | H |
| B1.31 | (N-methylcarbamoyl) | H |
| B1.32 | (N,N-dimethylcarbamoyl) | H |
| B1.33 | (N-phenylcarbamoyl) | H |
| B1.34 | —CN | H |
| B1.35 | H | methyl |
| B1.36 | ethyl | methyl |
| B1.37 | CH$_2$=CH—CH$_2$— | methyl |
| B1.38 | phenyl | methyl |
| B1.39 | Benzyl | methyl |
| B1.40 | (ethoxycarbonylmethyl) | methyl |
| B1.41 | (formyl) | methyl |
| B1.42 | (acetyl) | methyl |
| B1.43 | (acryloyl) | methyl |

TABLE B-continued

Compounds of the formula (I) and (II) wherein U is —N(R₂)OR₃ and R₂ and R₃ have the following meanings:

| No. | R₂ | R₃ |
|---|---|---|
| B1.44 | isobutyryl (CH(CH₃)₂-C(=O)-) | methyl |
| B1.45 | methoxyacetyl (CH₃O-CH₂-C(=O)-) | methyl |
| B1.46 | Benzoyl | Methyl |
| B1.47 | methoxycarbonyl (CH₃O-C(=O)-) | Methyl |
| B1.48 | dimethylaminocarbonyl ((CH₃)₂N-C(=O)-) | Methyl |
| B1.49 | phenylaminocarbonyl (PhNH-C(=O)-) | methyl |
| B1.50 | H | methyl |
| B1.51 | H | Ethyl |
| B1.52 | H | n-propyl |
| B1.53 | H | iso-propyl |
| B1.54 | H | n-butyl |
| B1.55 | H | s-butyl |
| B1.56 | H | iso-butyl |
| B1.57 | H | t-butyl |
| B1.58 | H | CH₂=CH—CH₂— |
| B1.59 | H | CH₃—CH=CH—CH₂— |
| B1.60 | H | HO—CH₂—CH₂— |
| B1.61 | H | phenyl |
| B1.62 | H | benzyl |
| B1.63 | H | phenethyl (-CH₂CH₂-C₆H₅) |
| B1.64 | H | -CH₂-C(=O)-O-Et |
| B1.65 | H | -CH₂-CH₂-C(=O)-O-Et |
| B1.66 | H | acetyl (CH₃-C(=O)-) |
| B1.67 | H | acetyl (CH₃-C(=O)-) |
| B1.68 | H | propionyl (CH₃CH₂-C(=O)-) |
| B1.69 | H | acryloyl (CH₂=CH-C(=O)-) |
| B1.70 | H | butyryl (CH₃CH₂CH₂-C(=O)-) |
| B1.71 | H | crotonyl (CH₃-CH=CH-C(=O)-) |
| B1.72 | H | isobutyryl ((CH₃)₂CH-C(=O)-) |
| B1.73 | H | methoxyacetyl (CH₃O-CH₂-C(=O)-) |
| B1.74 | H | ethoxyacetyl (CH₃CH₂O-CH₂-C(=O)-) |
| B1.75 | H | HO-CH₂CH₂-O-CH₂-C(=O)- |
| B1.76 | H | benzoyl (Ph-C(=O)-) |
| B1.77 | H | methoxycarbonyl (CH₃O-C(=O)-) |
| B1.78 | H | ethoxycarbonyl (CH₃CH₂O-C(=O)-) |
| B1.79 | H | aminocarbonyl (H₂N-C(=O)-) |
| B1.80 | H | methylaminocarbonyl (CH₃NH-C(=O)-) |

TABLE B-continued

Compounds of the formula (I) and (II) wherein U is —N(R₂)OR₃ and R₂ and R₃ have the following meanings:

| No. | R₂ | R₃ |
|---|---|---|
| B1.81 | H | -N(CH₃)₂-C(=O)- |
| B1.82 | H | PhNH-C(=O)- |
| B1.83 | H | —CN |
| B1.84 | methyl | H |
| B1.85 | methyl | Ethyl |
| B1.86 | methyl | CH₂=CH—CH₂— |
| B1.87 | methyl | phenyl |
| B1.88 | methyl | Benzyl |
| B1.89 | methyl | EtO-C(=O)- |
| B1.90 | methyl | H-C(=O)- |
| B1.91 | methyl | CH₃-C(=O)- |
| B1.92 | methyl | CH₂=CH-C(=O)- |
| B1.93 | methyl | (CH₃)₂CH-C(=O)- |
| B1.94 | methyl | CH₃O-CH₂-C(=O)- |
| B1.95 | methyl | benzoyl |
| B1.96 | methyl | CH₃O-C(=O)- |
| B1.97 | methyl | -N(CH₃)₂-C(=O)- |
| B1.98 | methyl | PhNH-C(=O)- |
| B1.99 | methyl | —CN |
| B1.100 | methyl | methyl |
| B1.101 | ethyl | Ethyl |
| B1.102 | ethyl | CH₂=CH—CH₂— |
| B1.103 | ethyl | H-C(=O)- |
| B1.104 | ethyl | CH₃-C(=O)- |
| B1.105 | ethyl | CH₃O-CH₂-C(=O)- |
| B1.106 | ethyl | CH₃O-C(=O)- |
| B1.107 | ethyl | —CN |
| B1.108 | CH₂=CH—CH₂— | Ethyl |
| B1.109 | H-C(=O)- | Ethyl |
| B1.110 | CH₃-C(=O)- | Ethyl |
| B1.111 | CH₃O-CH₂-C(=O)- | Ethyl |
| B1.112 | CH₃O-C(=O)- | Ethyl |
| B1.113 | —CN | Ethyl |
| B1.114 | CH₂=CH—CH₂— | CH₂=CH—CH₂— |
| B1.115 | CH₂=CH—CH₂— | H-C(=O)- |
| B1.116 | CH₂=CH—CH₂— | CH₃-C(=O)- |
| B1.117 | CH₂=CH—CH₂— | CH₃O-CH₂-C(=O)- |
| B1.118 | CH₂=CH—CH₂— | CH₃O-C(=O)- |
| B1.119 | CH₂=CH—CH₂— | —CN |

TABLE B-continued

Compounds of the formula (I) and (II) wherein U is —N(R$_2$)OR$_3$ and R$_2$ and R$_3$ have the following meanings:

| No. | R$_2$ | R$_3$ |
|---|---|---|
| B1.120 | H-C(=O)- | CH$_2$=CH—CH$_2$— |
| B1.121 | CH$_3$-C(=O)- | CH$_2$=CH—CH$_2$— |
| B1.122 | CH$_3$O-CH$_2$-C(=O)- | CH$_2$=CH—CH$_2$— |
| B1.123 | CH$_3$O-C(=O)- | CH$_2$=CH—CH$_2$— |
| B1.124 | —CN | CH$_2$=CH—CH$_2$— |
| B1.125 | —CH$_2$—CH$_2$—CH$_2$— | |
| B1.126 | —CH$_2$—CH$_2$—CH$_2$— | |
| B1.127 | isobutyl | |
| B1.128 | 3-methyl-but-2-enyl | |
| B1.129 | —CH$_2$CH$_2$CH(C(=O)OCH$_3$)— | |
| B1.130 | —CH$_2$CH$_2$CH(C(=O)OEt)— | |
| B1.131 | —CH$_2$CH$_2$CH(C(=O)NH$_2$)— | |
| B1.132 | —CH$_2$CH(CH$_3$)CH$_2$CH(C(=O)OCH$_3$)— | |
| B1.133 | —CH$_2$CH(CH$_3$)CH$_2$CH(C(=O)OEt)— | |
| B1.134 | —CH$_2$CH(CH$_3$)CH$_2$CH(C(=O)NH$_2$)— | |
| B1.135 | —CH=C(C(=O)OCH$_3$)CH$_2$— | |
| B1.136 | —CH=C(C(=O)OEt)CH$_2$— | |
| B1.137 | —CH=C(C(=O)OCH$_3$)CH(CH$_3$)— | |
| B1.138 | —CH=C(C(=O)OEt)CH(CH$_3$)— | |
| B1.139 | —CH$_2$CH$_2$CH(CN)— | |
| B1.140 | —CH$_2$CH(CH$_3$)CH$_2$CH(CN)— | |
| B1.141 | —C(C(=O)OEt)=C(C(=O)OEt)CH(CH$_3$)— | |
| B1.142 | —CH$_2$CH(CH$_3$)CH$_2$CH(CH$_2$OH)— | |
| B1.143 | —CH$_2$CH(CH$_3$)CH$_2$CH(CH$_2$OC(=O)CH$_3$)— | |

TABLE B-continued

Compounds of the formula (I) and (II) wherein U is —N(R$_2$)OR$_3$ and R$_2$ and R$_3$ have the following meanings:

| No. | R$_2$ | R$_3$ |
|---|---|---|
| B1.144 | | (isobutyl-CH-phenyl) |
| B1.145 | | (ethyl branched -CH-CN) |
| B1.146 | | (ethyl branched -CH-C(O)OEt) |
| B1.147 | | (ethyl branched =C(C(O)OEt)-C(O)OEt) |
| B1.148 | | (ethyl branched -CH-CH$_2$OH) |
| B1.149 | | (ethyl branched -CH-OC(O)CH$_3$) |
| B1.150 | | (ethyl branched -CH-phenyl) |
| B1.151 | | (cyclopentyl) |
| B1.152 | | (cyclopentenyl) |
| B1.153 | | (cyclohexyl) |
| B1.154 | | (cyclohexenyl) |
| B1.155 | | |
| B1.156 | | |
| B1.157 | | |
| B1.158 | | |
| B1.159 | | |
| B1.160 | | |

TABLE C

Compounds of the formula (I) wherein U is —N$^+$(O$^-$)=C(R$_E$)R$_Z$ and R$_E$ and R$_Z$ have the following meanings:

| No. | R$_E$ | R$_Z$ |
|---|---|---|
| C1.1 | H | H |
| C1.2 | methyl | H |
| C1.3 | ethyl | H |
| C1.4 | n-propyl | H |
| C1.5 | iso-propyl | H |
| C1.6 | n-butyl | H |
| C1.7 | s-butyl | H |
| C1.8 | iso-butyl | H |
| C1.9 | t-butyl | H |
| C1.10 | CH$_2$=CH—CH$_2$— | H |
| C1.11 | CH$_3$—CH=CH—CH$_2$— | H |
| C1.12 | phenyl | H |
| C1.13 | 2-methylphenyl | H |
| C1.14 | 3-methylphenyl | H |

TABLE C-continued

Compounds of the formula (I) wherein U is —N⁺(O⁻)═C(R$_E$)R$_Z$) and R$_E$ and R$_Z$ have the following meanings:

| | R$_E$ | R$_Z$ |
|---|---|---|
| C1.15 | 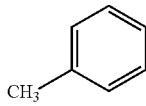 | H |
| C1.16 | 4-F-phenyl | H |
| C1.17 | 4-Cl-phenyl | H |
| C1.18 | 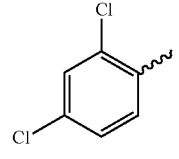 | H |
| C1.19 | 4-Br-phenyl | H |
| C1.20 | 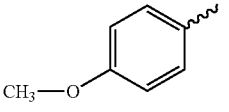 | H |
| C1.21 | 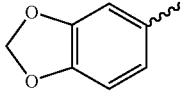 | H |
| C1.22 | 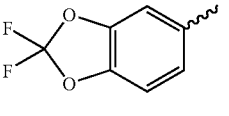 | H |
| C1.23 | CN | H |
| C1.24 | CF$_3$— | H |
| C1.25 | CCl$_3$— | H |
| C1.26 | CF$_3$—CH$_2$— | H |
| C1.27 | CF$_3$—CF$_2$— | H |
| C1.28 | CO$_2$—CH$_3$ | H |
| C1.29 | CO$_2$—C$_2$H$_5$ | H |
| C1.30 | HO—CH$_2$— | H |
| C1.31 | CO—NH$_2$ | H |
| C1.32 | CO—NH—CH$_3$ | H |
| C1.33 | CO—N(CH$_3$)$_2$ | H |
| C1.34 | CH3—O—CH$_2$— | H |
| C1.35 | C$_2$H$_5$—O—CH$_2$— | H |
| C1.36 | H | methyl |
| C1.37 | methyl | methyl |
| C1.38 | ethyl | methyl |
| C1.39 | n-propyl | methyl |
| C1.40 | iso-propyl | methyl |
| C1.41 | n-butyl | methyl |
| C1.42 | s-butyl | methyl |
| C1.43 | iso-butyl | methyl |
| C1.44 | t-butyl | methyl |
| C1.45 | CH$_2$=CH—CH$_2$— | methyl |
| C1.46 | CH$_3$—CH=CH—CH$_2$— | methyl |
| C1.47 | phenyl | methyl |
| C1.48 | 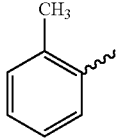 | methyl |
| C1.49 | 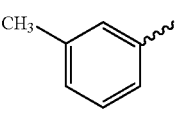 | methyl |
| C1.50 | 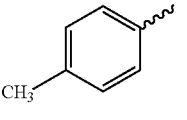 | methyl |
| C1.51 | 4-F-phenyl | methyl |
| C1.52 | 4-Cl-phenyl | methyl |
| C1.53 | 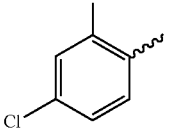 | methyl |
| C1.54 | 4-Br-phenyl | methyl |
| C1.55 | 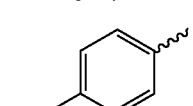 | methyl |
| C1.56 | 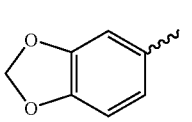 | methyl |
| C1.57 | 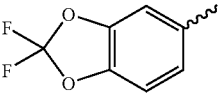 | methyl |
| C1.58 | CN | methyl |
| C1.59 | CF$_3$— | methyl |
| C1.60 | CCl$_3$— | methyl |
| C1.61 | CF$_3$—CH$_2$— | methyl |
| C1.62 | CF$_3$—CF$_2$— | methyl |
| C1.63 | CO$_2$—CH$_3$ | methyl |
| C1.64 | CO$_2$—C$_2$H$_5$ | methyl |
| C1.65 | HO—CH$_2$— | methyl |
| C1.66 | CO—NH$_2$ | methyl |
| C1.67 | CO—NH—CH$_3$ | methyl |
| C1.68 | CO—N(CH$_3$)$_2$ | methyl |
| C1.69 | CH3—O—CH$_2$— | methyl |
| C1.70 | C$_2$H$_5$—O—CH$_2$— | methyl |
| C1.71 | CN | CN |
| C1.72 | CF$_3$— | CF$_3$— |
| C1.73 | CCl$_3$— | CCl$_3$— |
| C1.74 | CN | CN |
| C1.75 | CO$_2$—CH$_3$ | CO$_2$—CH$_3$ |
| C1.76 | CO$_2$—C$_2$H$_5$ | CO$_2$—C$_2$H$_5$ |
| C1.77 | CO$_2$—C$_2$H$_5$ | CN |
| C1.78 | CN | CO$_2$—C$_2$H$_5$ |
| C1.79 | Phenyl | CF$_3$— |
| C1.80 | Phenyl | CN |
| C1.81 | —CH$_2$—CH$_2$—CH$_2$— | |
| C1.82 | —CH$_2$—CH$_2$—CH$_2$—CH$_2$— | |
| C1.83 | 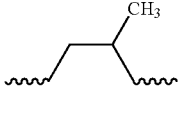 | |

TABLE C-continued

Compounds of the formula (I) wherein U is —N⁺(O⁻)=C(R_E)R_Z) and R_E and R_Z have the following meanings:

| | R_E | R_Z |
|---|---|---|
| C1.84 | | CH₂CH₃ branched |
| C1.85 | | CH(OH) with two chains |
| C1.86 | | C(OH)(CH₃) with two chains |
| C1.87 | | neopentyl-type |
| C1.88 | | CH(CH₃)CH₂ chain |
| C1.89 | | C(OH)(CH₃)CH₂ chain |
| C1.90 | | CH₂CH₂CH(CH₃) chain |
| C1.91 | | CH₂CH₂C(OH)(CH₃) chain |
| C1.92 | | C(CH₃)₂ with two chains |
| C1.93 | | CH₂C(CH₃)₂ with two chains |
| C1.94 | | cis-CH=CH linker |
| C1.95 | | CH₂C(CH₃)=CH chain |
| C1.96 | | CH(OH) with two chains |
| C1.97 | | CH₂CH(OH) chain |
| C1.98 | | CH(OH)CH(OH) chain |
| C1.99 | | cyclohexyl-type ring |
| C1.100 | | cycloheptyl-type ring |

Table Z1: A compound of the formula (II) in which the configuration of the C=N bond at the ε-position is E, G is H, n is 1, X—Y is —CH=CH—, R₁ is sec-butyl or isopropyl and R₃ for each compound corresponds to a line B1.1 to B1.160 of Table B.

Table Z2: A compound of the formula (II) in which the configuration of the C=N bond at the ε-position is Z, G is H, n is 1, X—Y is —CH=CH—, R₁ is sec-butyl (B1a) or isopropyl (B1b) and R₃ for each compound corresponds to a line B1.1 to B1.160 of Table B.

Table Z3: A compound of the formula (II) in which the configuration of the C=N bond at the ε-position is E, G is H, n is 1, X—Y is —CH₂—CH₂—, R₁ is sec-butyl (B1a) or isopropyl (B1b) and R₃ for each compound corresponds to a line B1.1 to B1.160 of Table B.

Table Z4: A compound of the formula (II) in which the configuration of the C=N bond at the ε-position is Z, G is H, n is 1, X—Y is —CH₂—CH₂—, R₁ is sec-butyl (B1a) or isopropyl (B1b) and R₃ for each compound corresponds to a line B1.1 to B1.160 of Table B.

Table Z5: A compound of the formula (II) in which the configuration of the C=N bond at the ε-position is E, G is H, n is 0, X—Y is —CH=CH—, R₁ is sec-butyl (B1a) or isopropyl (B1b) and R₃ for each compound corresponds to a line B1.1 to B1.160 of Table B.

Table Z6: A compound of the formula (II) in which the configuration of the C=N bond at the ε-position is Z, G is H, n is 0, X—Y is —CH═CH—, $R_1$ is sec-butyl (B1a) or isopropyl (B1b) and $R_3$ for each compound corresponds to a line B1.1 to B1.160 of Table B.

Table Z7: A compound of the formula (II) in which the configuration of the C═N bond at the ε-position is E, G is H, n is 0, X—Y is —CH$_2$—CH$_2$—, $R_1$ is sec-butyl (B1a) or isopropyl (B1b) and $R_3$ for each compound corresponds to a line B1.1 to B1.160 of Table B.

Table Z8: A compound of the formula (II) in which the configuration of the C═N bond at the ε-position is Z, G is H, n is 0, X—Y is —CH$_2$—CH$_2$—, $R_1$ is sec-butyl (B1a) or isopropyl (B1b) and $R_3$ for each compound corresponds to a line B1.1 to B1.160 of Table B.

Table Z9: A compound of the formula (II) in which the configuration of the C═N bond at the ε-position is E, G is H, n is 1, X—Y is —CH═CH—, $R_1$ cyclohexyl and $R_3$ for each compound corresponds to a line B1.1 to B1.160 of Table B.

Table Z10: A compound of the formula (II) in which the configuration of the C═N bond at the ε-position is Z, G is H, n is 1, X—Y is —CH═CH—, $R_1$ cyclohexyl and $R_3$ for each compound corresponds to a line B1.1 to B1.160 of Table B.

Table Z11: A compound of the formula (II) in which the configuration of the C═N bond at the ε-position is E, G is H, n is 1, X—Y is —CH$_2$—CH$_2$—, $R_1$ is cyclohexyl and $R_3$ for each compound corresponds to a line B1.1 to B1.160 of Table B.

Table Z12: A compound of the formula (II) in which the configuration of the C═N bond at the ε-position is Z, G is H, n is 1, X—Y is —CH$_2$—CH$_2$—, $R_1$ is cyclohexyl and $R_3$ for each compound corresponds to a line B1.1 to B1.160 of Table B.

Table Z13: A compound of the formula (II) in which the configuration of the C═N bond at the ε-position is E, G is H, n is 0, X—Y is —CH═CH—, $R_1$ is cyclohexyl and $R_3$ for each compound corresponds to a line B1.1 to B1.160 of Table B.

Table Z14: A compound of the formula (II) in which the configuration of the C═N bond at the ε-position is Z, G is H, n is 0, X—Y is —CH═CH—, $R_1$ is cyclohexyl and $R_3$ for each compound corresponds to a line B1.1 to B1.160 of Table B.

Table Z15: A compound of the formula (II) in which the configuration of the C═N bond at the ε-position is E, G is H, n is 0, X—Y is —CH$_2$—CH$_2$—, $R_1$ is cyclohexyl and $R_3$ for each compound corresponds to a line B1.1 to B1.160 of Table B.

Table Z16: A compound of the formula (II) in which the configuration of the C═N bond at the ε-position is Z, G is H, n is 0, X—Y is —CH$_2$—CH$_2$—, $R_1$ is cyclohexyl and $R_3$ for each compound corresponds to a line B1.1 to B1.160 of Table B.

Table Z17: A compound of the formula (II) in which the configuration of the C═N bond at the ε-position is E, G is H, n is 1, X—Y is —CH═CH—, $R_1$ is 1-methyl-butyl and $R_3$ for each compound corresponds to a line B1.1 to B1.160 of Table B.

Table Z18: A compound of the formula (II) in which the configuration of the C═N bond at the ε-position is Z, G is H, n is 1, X—Y is CH═CH—, $R_1$ is 1-methyl-butyl and $R_3$ for each compound corresponds to a line B1.1 to B1.160 of Table B.

Table Z19: A compound of the formula (II) in which the configuration of the C═N bond at the ε-position is E, G is H, n is 1, X—Y is —CH$_2$—CH$_2$—, $R_1$ is 1-methyl-butyl and $R_3$ for each compound corresponds to a line B1.1 to B1.160 of Table B.

Table Z20: A compound of the formula (II) in which the configuration of the C═N bond at the ε-position is Z, G is H, n is 1, X—Y is —CH$_2$—CH$_2$—, $R_1$ is 1-methyl-butyl and $R_3$ for each compound corresponds to a line B1.1 to B1.160 of Table B.

Table Z21: A compound of the formula (II) in which the configuration of the C═N bond at the ε-position is E, G is H, n is 0, X—Y is CH═CH—, $R_1$ is 1-methyl-butyl and $R_3$ for each compound corresponds to a line B1.1 to B1.160 of Table B.

Table Z22: A compound of the formula (II) in which the configuration of the C═N bond at the ε-position is Z, G is H, n is 0, X—Y is —CH═CH—, $R_1$ is 1-methyl-butyl and $R_3$ for each compound corresponds to a line B1.1 to B1.160 of Table B.

Table Z23: A compound of the formula (II) in which the configuration of the C═N bond at the ε-position is E, G is H, n is 0, X—Y is —CH$_2$—CH$_2$—, $R_1$ is 1-methyl-butyl and $R_3$ for each compound corresponds to a line B1.1 to B1.160 of Table B.

Table Z24: A compound of the formula (II) in which the configuration of the C═N bond at the ε-position is Z, G is H, n is 0, X—Y is —CH$_2$—CH$_2$—, $R_1$ is 1-methyl-butyl and $R_3$ for each compound corresponds to a line B1.1 to B1.160 of Table B.

Table Z25: A compound of the formula (II) in which the configuration of the C═N bond at the ε-position is E, G is t-butyl-dimethylsilyl, n is 1, X—Y is —CH═CH—, $R_1$ is sec-butyl (B1a) or isopropyl (B1b) and $R_3$ for each compound corresponds to a line B1.1 to B1.160 of Table B.

Table Z26: A compound of the formula (II) in which the configuration of the C═N bond at the ε-position is Z, G is t-butyl-dimethylsilyl, n is 1, X—Y is —CH═CH—, $R_1$ is sec-butyl (B1a) or isopropyl (B1b) and $R_3$ for each compound corresponds to a line B1.1 to B1.160 of Table B.

Table Z27: A compound of the formula (II) in which the configuration of the C═N bond at the ε-position is E, G is t-butyl-dimethylsilyl, n is 1, X—Y is —CH$_2$—CH$_2$—, $R_1$ is sec-butyl (B1a) or isopropyl (B1b) and $R_3$ for each compound corresponds to a line B1.1 to B1.160 of Table B.

Table Z28: A compound of the formula (II) in which the configuration of the C═N bond at the ε-position is Z, G is t-butyl-dimethylsilyl, n is 1, X—Y is —CH$_2$—CH$_2$—, $R_1$ is sec-butyl (B1a) or isopropyl (B1b) and $R_3$ for each compound corresponds to a line B1.1 to B1.160 of Table B.

Table Z29: A compound of the formula (II) in which the configuration of the C═N bond at the ε-position is E, G is t-butyl-dimethylsilyl, n is 0, X—Y is —CH═CH—, $R_1$ is sec-butyl (B1a) or isopropyl (B1b) and $R_3$ for each compound corresponds to a line B1.1 to B1.160 of Table B.

Table Z30: A compound of the formula (II) in which the configuration of the C═N bond at the ε-position is Z, G is t-butyl-dimethylsilyl, n is 0, X—Y is —CH═CH—, $R_1$ is sec-butyl (B1a) or isopropyl (B1b) and $R_3$ for each compound corresponds to a line B1.1 to B1.160 of Table B.

Table Z31: A compound of the formula (II) in which the configuration of the C=N bond at the ε-position is E, G is t-butyl-dimethylsilyl, n is 0, X—Y is —CH$_2$—CH$_2$—, R$_1$ is sec-butyl (B1a) or isopropyl (B1b) and R$_3$ for each compound corresponds to a line B1.1 to B1.160 of Table B.

Table Z32: A compound of the formula (II) in which the configuration of the C=N bond at the ε-position is Z, G is t-butyl-dimethylsilyl, n is 0, X—Y is —CH$_2$—CH$_2$—, R$_1$ is sec-butyl (B1a) or isopropyl (B1b) and R$_3$ for each compound corresponds to a line B1.1 to B1.160 of Table B.

Table Z33: A compound of the formula (II) in which the configuration of the C=N bond at the ε-position is E, G is t-butyl-dimethylsilyl, n is 1, X—Y is —CH=CH—, R$_1$ cyclohexyl and R$_3$ for each compound corresponds to a line B1.1 to B1.160 of Table B.

Table Z34: A compound of the formula (II) in which the configuration of the C=N bond at the ε-position is Z, G is t-butyl-dimethylsilyl, n is 1, X—Y is —CH=CH—, R$_1$ cyclohexyl and R$_3$ for each compound corresponds to a line B1.1 to B1.160 of Table B.

Table Z35: A compound of the formula (II) in which the configuration of the C=N bond at the ε-position is E, G is t-butyl-dimethylsilyl, n is 1, X—Y is —CH$_2$=CH$_2$—, R$_1$ is cyclohexyl and R$_3$ for each compound corresponds to a line B1.1 to B1.160 of Table B.

Table Z36: A compound of the formula (II) in which the configuration of the C=N bond at the ε-position is Z, G is t-butyl-dimethylsilyl, n is 1, X—Y is —CH$_2$—CH$_2$—, R$_1$ cyclohexyl and R$_3$ for each compound corresponds to a line B1.1 to B1.160 of Table B.

Table Z37: A compound of the formula (II) in which the configuration of the C=N bond at the ε-position is E, G is t-butyl-dimethylsilyl, n is 0, X—Y is —CH=CH—, R$_1$ is cyclohexyl and R$_3$ for each compound corresponds to a line B1.1 to B1.160 of Table B.

Table Z38: A compound of the formula (II) in which the configuration of the C=N bond at the ε-position is Z, G is t-butyl-dimethylsilyl, n is 0, X—Y is —CH=CH—, R$_1$ cyclohexyl and R$_3$ for each compound corresponds to a line B1.1 to B1.160 of Table B.

Table Z39: A compound of the formula (II) in which the configuration of the C=N bond at the ε-position is E, G is t-butyl-dimethylsilyl, n is 0, X—Y is —CH$_2$—CH$_2$—, R$_1$ is cyclohexyl and R$_3$ for each compound corresponds to a line B1.1 to B1.160 of Table B.

Table Z40: A compound of the formula (II) in which the configuration of the C=N bond at the ε-position is Z, G is t-butyl-dimethylsilyl, n is 0, X—Y is —CH$_2$—CH$_2$—, R$_1$ is cyclohexyl and R$_3$ for each compound corresponds to a line B1.1 to B1.160 of Table B.

Table Z41: A compound of the formula (II) in which the configuration of the C=N bond at the ε-position is E, G is t-butyl-dimethylsilyl, n is 1, X—Y is —CH=CH—, R$_1$ is 1-methyl-butyl and R$_3$ for each compound corresponds to a line B1.1 to B1.160 of Table B.

Table Z42: A compound of the formula (II) in which the configuration of the C=N bond at the ε-position is Z, G is t-butyl-dimethylsilyl, n is 1, X—Y is —CH=CH—, R$_1$ is 1-methyl-butyl and R$_3$ for each compound corresponds to a line B1.1 to B1.160 of Table B.

Table Z43: A compound of the formula (II) in which the configuration of the C=N bond at the ε-position is E, G is t-butyl-dimethylsilyl, n is 1, X—Y is —CH$_2$—CH$_2$—, R$_1$ is 1-methyl-butyl and R$_3$ for each compound corresponds to a line B1.1 to B1.160 of Table B.

Table Z44: A compound of the formula (II) in which the configuration of the C=N bond at the ε-position is Z, G is t-butyl-dimethylsilyl, n is 1, X—Y is —CH$_2$—CH$_2$—, R$_1$ is 1-methyl-butyl and R$_3$ for each compound corresponds to a line B1.1 to B1.160 of Table B.

Table Z45: A compound of the formula (II) in which the configuration of the C=N bond at the ε-position is E, G is t-butyl-dimethylsilyl, n is 0, X—Y is —CH=CH—, R$_1$ is 1-methyl-butyl and R$_3$ for each compound corresponds to a line B1.1 to B1.160 of Table B.

Table Z46: A compound of the formula (II) in which the configuration of the C=N bond at the ε-position is Z, G is t-butyl-dimethylsilyl, n is 0, X—Y is —CH=CH—, R$_1$ is 1-methyl-butyl and R$_3$ for each compound corresponds to a line B1.1 to B1.160 of Table B.

Table Z47: A compound of the formula (II) in which the configuration of the C=N bond at the ε-position is E, G is t-butyl-dimethylsilyl, n is 0, X—Y is —CH$_2$—CH$_2$—, R$_1$ is 1-methyl-butyl and R$_3$ for each compound corresponds to a line B1.1 to B1.160 of Table B.

Table Z48: A compound of the formula (II) in which the configuration of the C=N bond at the ε-position is Z, G is t-butyl-dimethylsilyl, n is 0, X—Y is —CH$_2$—CH$_2$—, R$_1$ is 1-methyl-butyl and R$_3$ for each compound corresponds to a line B1.1 to B1.160 of Table Z49: A compound of the formula (III) in which the configuration of the ε-position is (R), G is H, n is 1, X—Y is —CH=CH—, R$_1$ is sec-butyl (B1a) or isopropyl (B1b) and the combination of R$_Z$ and R$_E$ for each compound corresponds to a line C1.1 to C1.100 of Table C.

Table Z50: A compound of the formula (III) in which the configuration of the ε-position is (S), G is H, n is 1, X—Y is —CH=CH—, R$_1$ is sec-butyl (B1a) or isopropyl (B1b) and the combination of R$_Z$ and R$_E$ for each compound corresponds to a line C1.1 to C1.100 of Table C.

Table Z51: A compound of the formula (III) in which the configuration of the ε-position is (R), G is H, n is 1, X—Y is —CH$_2$—CH$_2$—, R$_1$ is sec-butyl (B1a) or isopropyl (B1b) and the combination of R$_Z$ and R$_E$ for each compound corresponds to a line C1.1 to C1.100 of Table C.

Table Z52: A compound of the formula (III) in which the configuration of the ε-position is (S), G is H, n is 1, X—Y is —CH$_2$—CH$_2$—, R$_1$ is sec-butyl (B1a) or isopropyl (B1b) and the combination of R$_Z$ and R$_E$ for each compound corresponds to a line C1.1 to C1.100 of Table C.

Table Z53: A compound of the formula (III) in which the configuration of the ε-position is (R), G is H, n is 0, X—Y is —CH=CH—, R$_1$ is sec-butyl (B1a) or isopropyl (B1b) and the combination of R$_Z$ and R$_E$ for each compound corresponds to a line C1.1 to C1.100 of Table C.

Table Z54: A compound of the formula (III) in which the configuration of the ε-position is (S), G is H, n is 0, X—Y is —CH=CH—, R$_1$ is sec-butyl (B1a) or isopropyl (B1b) and the combination of R$_Z$ and R$_E$ for each compound corresponds to a line C1.1 to C1.100 of Table C.

Table Z55: A compound of the formula (III) in which the configuration of the ε-position is (R), G is H, n is 0, X—Y is —CH$_2$—CH$_2$—, R$_1$ is sec-butyl (B1a) or isopropyl (B1b) and the combination of R$_Z$ and R$_E$ for each compound corresponds to a line C1.1 to C1.100 of Table C.

Table Z56: A compound of the formula (III) in which the configuration of the ε-position is (S), G is H, n is 0, X—Y is —CH$_2$—CH$_2$—, R$_1$ is sec-butyl (B1a) or isopropyl (B1b) and the combination of R$_Z$ and R$_E$ for each compound corresponds to a line C1.1 to C1.100 of Table C.

Table Z57: A compound of the formula (III) in which the configuration of the ε-position is (R), G is H, n is 1, X—Y is —CH=CH—, R$_1$ cyclohexyl and the combination of R$_Z$ and R$_E$ for each compound corresponds to a line C1.1 to C1.100 of Table C.

Table Z58: A compound of the formula (III) in which the configuration of the ε-position is (S), G is H, n is 1, X—Y is —CH=CH—, R$_1$ cyclohexyl and the combination of R$_Z$ and R$_E$ for each compound corresponds to a line C1.1 to C1.100 of Table C.

Table Z59: A compound of the formula (III) in which the configuration of the ε-position is (R), G is H, n is 1, X—Y is —CH$_2$—CH$_2$—, R$_1$ is cyclohexyl and the combination of R$_Z$ and R$_E$ for each compound corresponds to a line C1.1 to C1.100 of Table C.

Table Z60: A compound of the formula (III) in which the configuration of the ε-position is (S), G is H, n is 1, X—Y is —CH$_2$—CH$_2$—, R$_1$ is cyclohexyl and the combination of R$_Z$ and R$_E$ for each compound corresponds to a line C1.1 to C1.100 of Table C.

Table Z61: A compound of the formula (III) in which the configuration of the ε-position is (R), G is H, n is 0, X—Y is —CH=CH—, R$_1$ is cyclohexyl and the combination of R$_Z$ and R$_E$ for each compound corresponds to a line C1.1 to C1.100 of Table C.

Table Z62: A compound of the formula (III) in which the configuration of the ε-position is (S), G is H, n is 0, X—Y is —CH=CH—, R$_1$ is cyclohexyl and the combination of R$_Z$ and R$_E$ for each compound corresponds to a line C1.1 to C1.100 of Table C.

Table Z63: A compound of the formula (III) in which the configuration of the ε-position is (R), G is H, n is 0, X—Y is —CH$_2$—CH$_2$—, R$_1$ is cyclohexyl and the combination of R$_Z$ and R$_E$ for each compound corresponds to a line C1.1 to C1.100 of Table C.

Table Z64: A compound of the formula (III) in which the configuration of the ε-position is (S), G is H, n is 0, X—Y is —CH$_2$—CH$_2$—, R$_1$ is cyclohexyl and the combination of R$_Z$ and R$_E$ for each compound corresponds to a line C1.1 to C1.100 of Table C.

Table Z65: A compound of the formula (III) in which the configuration of the ε-position is (R), G is H, n is 1, X—Y is —CH=CH—, R$_1$ is 1-methyl-butyl and the combination of R$_Z$ and R$_E$ for each compound corresponds to a line C1.1 to C1.100 of Table C.

Table Z66: A compound of the formula (III) in which the configuration of the ε-position is (S), G is H, n is 1, X—Y is —CH=CH—, R$_1$ is 1-methyl-butyl and the combination of R$_Z$ and R$_E$ for each compound corresponds to a line C1.1 to C1.100 of Table C.

Table Z67: A compound of the formula (III) in which the configuration of the ε-position is (R), G is H, n is 1, X—Y is —CH$_2$—CH$_2$—, R$_1$ is 1-methyl-butyl and the combination of R$_Z$ and R$_E$ for each compound corresponds to a line C1.1 to C1.100 of Table C.

Table Z68: A compound of the formula (III) in which the configuration of the ε-position is (S), G is H, n is 1, X—Y is —CH$_2$—CH$_2$—, R$_1$ is 1-methyl-butyl and the combination of R$_Z$ and R$_E$ for each compound corresponds to a line C1.1 to C1.100 of Table C.

Table Z69: A compound of the formula (III) in which the configuration of the ε-position is (R), G is H, n is 0, X—Y is —CH=CH—, R$_1$ is 1-methyl-butyl and the combination of R$_Z$ and R$_E$ for each compound corresponds to a line C1.1 to C1.100 of Table C.

Table Z70: A compound of the formula (III) in which the configuration of the ε-position is (S), G is H, n is 0, X—Y is —CH=CH—, R$_1$ is 1-methyl-butyl and the combination of R$_Z$ and R$_E$ for each compound corresponds to a line C1.1 to C1.100 of Table C.

Table Z71: A compound of the formula (III) in which the configuration of the ε-position is (R), G is H, n is 0, X—Y is —CH$_2$—CH$_2$—, R$_1$ is 1-methyl-butyl and the combination of R$_Z$ and R$_E$ for each compound corresponds to a line C1.1 to C1.100 of Table C.

Table Z72: A compound of the formula (III) in which the configuration of the ε-position is (S), G is H, n is 0, X—Y is —CH$_2$—CH$_2$—, R$_1$ is 1-methyl-butyl and the combination of R$_Z$ and R$_E$ for each compound corresponds to a line C1.1 to C1.100 of Table C.

Table 1: A Compound of the formula (Ib) wherein the configuration at the ε-position is (S), G is H, n is 1, X—Y is —CH=CH—, R$_1$ is sec-butyl or isopropyl and the combination of R$_2$ and R$_3$ for each compound corresponds to a line B1.1 to B1.160 of Table B.

Table 2: A Compound of the formula (Ib) wherein the configuration at the ε-position is (R), G is H, n is 1, X—Y is —CH=CH—, R$_1$ is sec-butyl or isopropyl and the combination of R$_2$ and R$_3$ for each compound corresponds to a line B1.1 to B1.160 of Table B.

Table 3: A Compound of the formula (Ib) wherein the configuration at the ε-position is (S), G is H, n is 1, X—Y is —CH$_2$—CH$_2$—, R$_1$ is sec-butyl or isopropyl and the combination of R$_2$ and R$_3$ for each compound corresponds to a line B1.1 to B1.160 of Table B.

Table 4: A Compound of the formula (Ib) wherein the configuration at the ε-position is (R), G is H, n is 1, X—Y is —CH$_2$—CH$_2$—, R$_1$ is sec-butyl or isopropyl and the combination of R$_2$ and R$_3$ for each compound corresponds to a line B1.1 to B1.160 of Table B.

Table 5: A Compound of the formula (Ib) wherein the configuration at the ε-position is (S), G is H, n is 0, X—Y is —CH=CH—, R$_1$ is sec-butyl or isopropyl and the combination of R$_2$ and R$_3$ for each compound corresponds to a line B1.1 to B1.160 of Table B.

Table 6: A Compound of the formula (Ib) wherein the configuration at the ε-position is (R) G is H, n is 0, X—Y is —CH=CH—, R$_1$ is sec-butyl or isopropyl and the combination of R$_2$ and R$_3$ for each compound corresponds to a line B1.1 to B1.160 of Table B.

Table 7: A Compound of the formula (Ib) wherein the configuration at the ε-position is (S), G is H, n is 0, X—Y is —$CH_2$—$CH_2$—, $R_1$ is sec-butyl or isopropyl and the combination of $R_2$ and $R_3$ for each compound corresponds to a line B1.1 to B1.160 of Table B.

Table 8: A Compound of the formula (Ib) wherein the configuration at the ε-position is (R), G is H, n is 0, X—Y is —$CH_2$—$CH_2$—, $R_1$ is sec-butyl or isopropyl and the combination of $R_2$ and $R_3$ for each compound corresponds to a line B1.1 to B1.160 of Table B.

Table 9: A Compound of the formula (Ia) wherein the configuration at the ε-position is (S), G is H, n is 1, X—Y is —CH=CH—, $R_1$ is sec-butyl or isopropyl and the combination of $R_Z$ and $R_E$ for each compound corresponds to a line C1.1 to C1.100 of Table C.

Table 10: A Compound of the formula (Ia) wherein the configuration at the ε-position is (R), G is H, n is 1, X—Y is —CH=CH—, $R_1$ is sec-butyl or isopropyl and the combination of $R_Z$ and $R_E$ for each compound corresponds to a line C1.1 to C1.100 of Table C.

Table 11: A Compound of the formula (Ia) wherein the configuration at the ε-position is (S), G is H, n is 1, X—Y is —$CH_2$—$CH_2$—, $R_1$ is sec-butyl or isopropyl and the combination of $R_Z$ and $R_E$ for each compound corresponds to a line C1.1 to C1.100 of Table C.

Table 12: A Compound of the formula (Ia) wherein the configuration at the ε-position is (R), G is H, n is 1, X—Y is —$CH_2$—$CH_2$—, $R_1$ is sec-butyl or isopropyl and the combination of $R_Z$ and $R_E$ for each compound corresponds to a line C1.1 to C1.100 of Table C.

Table 13: A Compound of the formula (Ia) wherein the configuration at the ε-position is (S), G is H, n is 0, X—Y is —CH=CH—, $R_1$ is sec-butyl or isopropyl and the combination of $R_Z$ and $R_E$ for each compound corresponds to a line C1.1 to C1.100 of Table C.

Table 14: A Compound of the formula (Ia) wherein the configuration at the ε-position is (R) G is H, n is 0, X—Y is —CH=CH—, $R_1$ is sec-butyl or isopropyl and the combination of $R_Z$ and $R_E$ for each compound corresponds to a line C1.1 to C1.100 of Table C.

Table 15: A Compound of the formula (Ia) wherein the configuration at the ε-position is (S), G is H, n is 0, X—Y is —$CH_2$—$CH_2$—, $R_1$ is sec-butyl or isopropyl and the combination of $R_Z$ and $R_E$ for each compound corresponds to a line C1.1 to C1.100 of Table C.

Table 16: A Compound of the formula (Ia) wherein the configuration at the ε-position is (R), G is H, n is 0, X—Y is —$CH_2$—$CH_2$—, $R_1$ is sec-butyl or isopropyl and the combination of $R_Z$ and $R_E$ for each compound corresponds to a line C1.1 to C1.100 of Table C.

Table 17: A Compound of the formula (Ib) wherein the configuration at the ε-position is (S), G is H, n is 1, X—Y is —CH=CH—, $R_1$ is cyclohexyl and the combination of $R_2$ and $R_3$ for each compound corresponds to a line B1.1 to B1.160 of Table B.

Table 18: A Compound of the formula (Ib) wherein the configuration at the ε-position is (R), G is H, n is 1, X—Y is —CH=CH—, $R_1$ is cyclohexyl and the combination of $R_2$ and $R_3$ for each compound corresponds to a line B1.1 to B1.160 of Table B.

Table 19: A Compound of the formula (Ib) wherein the configuration at the ε-position is (S), G is H, n is 1, X—Y is —$CH_2$—$CH_2$—, $R_1$ is cyclohexyl and the combination of $R_2$ and $R_3$ for each compound corresponds to a line B1.1 to B1.160 of Table B.

Table 20: A Compound of the formula (Ib) wherein the configuration at the ε-position is (R), G is H, n is 1, X—Y is —$CH_2$—$CH_2$—, $R_1$ is cyclohexyl and the combination of $R_2$ and $R_3$ for each compound corresponds to a line B1.1 to B1.160 of Table B.

Table 21: A Compound of the formula (Ib) wherein the configuration at the ε-position is (S), G is H, n is 0, X—Y is —CH=CH—, $R_1$ is cyclohexyl and the combination of $R_2$ and $R_3$ for each compound corresponds to a line B1.1 to B1.160 of Table B.

Table 22: A Compound of the formula (Ib) wherein the configuration at the ε-position is (R), G is H, n is 0, X—Y is —CH=CH—, $R_1$ is cyclohexyl and the combination of $R_2$ and $R_3$ for each compound corresponds to a line B1.1 to B1.160 of Table B.

Table 23: A Compound of the formula (Ib) wherein the configuration at the ε-position is (S), G is H, n is 0, X—Y is —$CH_2$—$CH_2$—, $R_1$ is cyclohexyl and the combination of $R_2$ and $R_3$ for each compound corresponds to a line B1.1 to B1.160 of Table B.

Table 24: A Compound of the formula (Ib) wherein the configuration at the ε-position is (R), G is H, n is 0, X—Y is —$CH_2$—$CH_2$—, $R_1$ is cyclohexyl and the combination of $R_2$ and $R_3$ for each compound corresponds to a line B1.1 to B1.160 of Table B.

Table 25: A Compound of the formula (Ia) wherein the configuration at the ε-position is (S), G is H, n is 1, X—Y is —CH=CH—, $R_1$ is cyclohexyl and the combination of $R_Z$ and $R_E$ for each compound corresponds to a line C1.1 to C1.100 of Table C.

Table 26: A Compound of the formula (Ia) wherein the configuration at the ε-position is (R), G is H, n is 1, X—Y is —CH=CH—, $R_1$ is cyclohexyl and the combination of $R_Z$ and $R_E$ for each compound corresponds to a line C1.1 to C1.100 of Table C.

Table 27: A Compound of the formula (Ia) wherein the configuration at the ε-position is (S), G is H, n is 1, X—Y is —$CH_2$—$CH_2$—, $R_1$ is cyclohexyl and the combination of $R_Z$ and $R_E$ for each compound corresponds to a line C1.1 to C1.100 of Table C.

Table 28: A Compound of the formula (Ia) wherein the configuration at the ε-position is (R), G is H, n is 1, X—Y is —$CH_2$—$CH_2$—, $R_1$ is cyclohexyl and the combination of $R_Z$ and $R_E$ for each compound corresponds to a line C1.1 to C1.100 of Table C.

Table 29: A Compound of the formula (Ia) wherein the configuration at the ε-position is (S), G is H, n is 0, X—Y is —CH=CH—, $R_1$ is cyclohexyl and the combination of $R_Z$ and $R_E$ for each compound corresponds to a line C1.1 to C1.100 of Table C.

Table 30: A Compound of the formula (Ia) wherein the configuration at the ε-position is (R) G is H, n is 0, X—Y is —CH=CH—, $R_1$ is cyclohexyl and the combination of $R_Z$ and $R_E$ for each compound corresponds to a line C1.1 to C1.100 of Table C.

Table 31: A Compound of the formula (Ia) wherein the configuration at the ε-position is (S), G is H, n is 0, X—Y is —CH$_2$—CH$_2$—, R$_1$ is cyclohexyl and the combination of R$_Z$ and R$_E$ for each compound corresponds to a line C1.1 to C1.100 of Table C.

Table 32: A Compound of the formula (Ia) wherein the configuration at the ε-position is (R), G is H, n is 0, X—Y is —CH$_2$—CH$_2$—, R$_1$ is cyclohexyl and the combination of R$_Z$ and R$_E$ for each compound corresponds to a line C1.1 to C1.100 of Table C.

Table 33: A Compound of the formula (Ib) wherein the configuration at the ε-position is (S), G is H, n is 1, X—Y is —CH=CH—, R$_1$ is 1-methyl-butyl and the combination of R$_2$ and R$_3$ for each compound corresponds to a line B1.1 to B1.160 of Table B.

Table 34: A Compound of the formula (Ib) wherein the configuration at the ε-position is (R), G is H, n is 1, X—Y is —CH=CH—, R$_1$ is 1-methyl-butyl and the combination of R$_2$ and R$_3$ for each compound corresponds to a line B1.1 to B1.160 of Table B.

Table 35: A Compound of the formula (Ib) wherein the configuration at the ε-position is (S), G is H, n is 1, X—Y is —CH$_2$—CH$_2$—, R$_1$ is 1-methyl-butyl and the combination of R$_2$ and R$_3$ for each compound corresponds to a line B1.1 to B1.160 of Table B.

Table 36: A Compound of the formula (Ib) wherein the configuration at the ε-position is (R), G is H, n is 1, X—Y is —CH$_2$—CH$_2$—, R$_1$ is 1-methyl-butyl and the combination of R$_2$ and R$_3$ for each compound corresponds to a line B1.1 to B1.160 of Table B.

Table 37: A Compound of the formula (Ib) wherein the configuration at the ε-position is (S), G is H, n is 0, X—Y is —CH=CH—, R$_1$ is 1-methyl-butyl and the combination of R$_2$ and R$_3$ for each compound corresponds to a line B1.1 to B1.160 of Table B.

Table 38: A Compound of the formula (Ib) wherein the configuration at the ε-position is (R) G is H, n is 0, X—Y is —CH=CH—, R$_1$ is 1-methyl-butyl and the combination of R$_2$ and R$_3$ for each compound corresponds to a line B1.1 to B1.160 of Table B.

Table 39: A Compound of the formula (Ib) wherein the configuration at the ε-position is (S), G is H, n is 0, X—Y is —CH$_2$—CH$_2$—, R$_1$ is 1-methyl-butyl and the combination of R$_2$ and R$_3$ for each compound corresponds to a line B1.1 to B1.160 of Table B.

Table 40: A Compound of the formula (Ib) wherein the configuration at the ε-position is (R), G is H, n is 0, X—Y is —CH$_2$—CH$_2$—, R$_1$ is 1-methyl-butyl and the combination of R$_2$ and R$_3$ for each compound corresponds to a line B1.1 to B1.160 of Table B.

Table 41: A Compound of the formula (Ia) wherein the configuration at the ε-position is (S), G is H, n is 1, X—Y is —CH=CH—, R$_1$ is 1-methyl-butyl and the combination of R$_Z$ and R$_E$ for each compound corresponds to a line C1.1 to C1.100 of Table C.

Table 42: A Compound of the formula (Ia) wherein the configuration at the ε-position is (R), G is H, n is 1, X—Y is —CH=CH—, R$_1$ is 1-methyl-butyl and the combination of R$_Z$ and R$_E$ for each compound corresponds to a line C1.1 to C1.100 of Table C.

Table 43: A Compound of the formula (Ia) wherein the configuration at the ε-position is (S), G is H, n is 1, X—Y is —CH$_2$—CH$_2$—, R$_1$ is 1-methyl-butyl and the combination of R$_Z$ and R$_E$ for each compound corresponds to a line C1.1 to C1.100 of Table C.

Table 44: A Compound of the formula (Ia) wherein the configuration at the ε-position is (R), G is H, n is 1, X—Y is —CH$_2$—CH$_2$—, R$_1$ is 1-methyl-butyl and the combination of R$_Z$ and R$_E$ for each compound corresponds to a line C1.1 to C1.100 of Table C.

Table 45: A Compound of the formula (Ia) wherein the configuration at the ε-position is (S), G is H, n is 0, X—Y is —CH=CH—, R$_1$ is 1-methyl-butyl and the combination of R$_Z$ and R$_E$ for each compound corresponds to a line C1.1 to C1.100 of Table C.

Table 46: A Compound of the formula (Ia) wherein the configuration at the ε-position is (R) G is H, n is 0, X—Y is —CH=CH—, R$_1$ is 1-methyl-butyl and the combination of R$_Z$ and R$_E$ for each compound corresponds to a line C1.1 to C1.100 of Table C.

Table 47: A Compound of the formula (Ia) wherein the configuration at the ε-position is (S), G is H, n is 0, X—Y is —CH$_2$—CH$_2$—, R$_1$ is 1-methyl-butyl and the combination of R$_Z$ and R$_E$ for each compound corresponds to a line C1.1 to C1.100 of Table C.

Table 48: A Compound of the formula (Ia) wherein the configuration at the ε-position is (R), G is H, n is 0, X—Y is —CH$_2$—CH$_2$—, R$_1$ is 1-methyl-butyl and the combination of R$_Z$ and R$_E$ for each compound corresponds to a line C1.1 to C1.100 of Table C.

Formulation Examples for Use in Crop Protection
(% is Percent by Weight)

Example F1: Emulsion concentrates

|  | a) | b) | c) |
| --- | --- | --- | --- |
| Active compound | 25% | 40% | 50% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing of finely ground active compound and additives gives an emulsion concentrate which, by dilution with water, affords emulsions of the desired concentration.

Example F2: Solutions

|  | a) | b) | c) | d) |
| --- | --- | --- | --- | --- |
| Active compound | 80% | 10% | 5% | 95% |
| Ethylene glycol monomethyl ether | — | 20% | — | — |
| Polyethylene glycol (MW 400) | — | 70% | — | — |
| N-methylpyrrolid-2-one | 20% | — | — | — |

Example F2: Solutions

|  | a) | b) | c) | d) |
|---|---|---|---|---|
| Epoxidized coconut oil | — | — | 1% | 5% |
| Petroleum ether (boiling range: 160-190°) | — | — | 94% | — |

Mixing of finely ground active compound and additives gives a solution suitable for use in the form of microdrops.

Example F3: Granules

|  | a) | b) | c) | d) |
|---|---|---|---|---|
| Active compound | 5% | 10% | 8% | 21% |
| Kaolin | 94% | — | 79% | 54% |
| Finely divided silicic acid | 1% | — | 13% | 7% |
| Attapulgite | — | 90% | — | 18% |

The active compound is dissolved in dichloromethane, the solution is sprayed onto the mixture of carriers and the solvent is evaporated under reduced pressure.

Example F4: Wettable powder

|  | a) | b) | c) |
|---|---|---|---|
| Active compound | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Active compound and additives are mixed and the mixture is ground in a suitable mill. This gives wettable powders which can be diluted with water to give suspensions of the desired concentration.

Example F5: Emulsion concentrate

| Active compound | 10% |
|---|---|
| Octylphenol polyethylene glycol ether (4-5 mol of EO) | 3% |
| Calcium dodecylbenzenesulphonate | 3% |
| Castor oil polyethylene glycol ether (36 mol of EO) | 4% |
| Cyclohexanone | 30% |
| Xylene mixture | 50% |

Mixing of finely ground active compound and additives gives an emulsion concentrate which, by dilution with water, affords emulsions of the desired concentration.

Example F6: Extruder granules

| Active compound | 10% |
|---|---|
| Sodium lignosulphonate | 2% |
| Carboxymethylcellulose | 1% |
| Kaolin | 87% |

Active compound and additives are mixed, the mixture is ground, moistened with water, extruded and granulated, and the granules are dried in a stream of air.

Example 7: Coated granules

| Active compound | 3% |
|---|---|
| Polyethylene glycol (MW 200) | 3% |
| Kaolin | 94% |

In a mixer, the finely ground active compound is applied uniformly to the kaolin which has been moistened with polyethylene glycol. This gives dust-free coated granules.

Example F8: Suspension Concentrate

| Example F8: Suspension concentrate | |
|---|---|
| Active compound | 40% |
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground active compound and additives gives a suspension concentrate which, by dilution with water, affords suspensions of the desired concentration.

Biological Examples

Example B1

Activity Against *Spodoptera littoralis*

Young soya bean plants are sprayed with an aqueous emulsion spray liquor which comprises 12.5 ppm of active compound, and, after the spray coating has dried on, populated with 10 caterpillars of the first stage of *Spodoptera littoralis* and introduced into a plastic container. 3 days later, the reduction in the population in percent and the reduction in the feeding damage in percent (% activity) are determined by comparing the number of dead caterpillars and the feeding damage between the treated and the untreated plants.

In this test, the compounds of the Tables A1 to A8 and Tables 1 to 48 show good activity. Thus, in particular the compounds A1.1 to A8.1 are more than 80% effective.

Example B2

Activity Against *Spodoptera littoralis*, Systemic

Maize seedlings are placed into the test solution which comprises 12.5 ppm of active compound. After 6 days, the leaves are cut off, placed onto moist filter paper in a Petri dish and populated with 12 to 15 *Spodoptera littoralis* larvae of the $L_1$ stage. 4 days later, the reduction of the population in percent (% activity) is determined by comparing the number of dead caterpillars between the treated and the untreated plants.

In this test, the compounds of the Tables A1 to A8 and Tables 1 to 48 show good activity. Thus, in particular the compounds A1.1 to A8.1 are more than 80% effective.

Example B3

Activity Against *Heliothis virescens*

30-35 0- to 24-hour-old eggs of *Heliothis virescens* are placed onto filter paper in a Petri dish on a layer of synthetic feed. 0.8 ml of the test solution which comprises 12.5 ppm of active compound is then pipetted onto the filter papers. Evaluation is carried out after 6 days. The reduction in the population in percent (% activity) is determined by comparing the number of dead eggs and larvae on the treated and the untreated filter papers.

In this test, the compounds of the Tables A1 to A8 and Tables 1 to 48 show good activity. Thus, in particular the compounds A1.1 to A8.1 are more than 80% effective.

Example B4

Activity Against *Plutella xylostella* Caterpillars

Young cabbage plants are sprayed with an aqueous emulsion spray liquor which comprises 12.5 ppm of the active compound. After the spray coating has dried on, the cabbage plants are populated with 10 caterpillars of the first stage of *Plutella xylostella* and introduced into a plastic container. Evaluation is carried out after 3 days. The reduction in the population in percent and the reduction in the feeding damage in percent (% activity) are determined by comparing the number of dead caterpillars and the feeding damage on the treated and the untreated plants.

In this test, the compounds of the Tables A1 to A8 and Tables 1 to 48 show good activity. Thus, in particular the compounds A1.1 to A8.1 are more than 80% effective.

Example B5

Activity Against *Frankliniella occidentalis*

In Petri dishes, discs of the leaves of beans are placed onto agar and sprayed with test solution which comprises 12.5 ppm of active compound in a spraying chamber. The leaves are then populated with a mixed population of *Frankliniella occidentalis*. Evaluation is carried out after 10 days. The reduction in percent (% activity) is determined by comparing the population on the treated leaves with that of the untreated leaves.

In this test, the compounds of the Tables A1 to A8 and Tables 1 to 48 show good activity. Thus, in particular the compounds A1.1 to A8.1 are more than 80% effective.

Example B6

Activity Against *Diabrotica balteata*

Maize seedlings are sprayed with an aqueous emulsion spray liquor which comprises 12.5 ppm of active compound and, after the spray coating has dried on, populated with 10 larvae of the second stage of *Diabrotica balteata* and then introduced into a plastic container. After 6 days, the reduction in the population in percent (% activity) is determined by comparing the dead larvae between the treated and the untreated plants.

In this test, the compounds of the Tables A1 to A8 and Tables 1 to 48 show good activity. Thus, in particular the compounds A1.1 to A8.1 are more than 80% effective.

Example B7

Activity Against *Tetranychus urticae*

Young bean plants are populated with a mixed population of *Tetranychus urticae* and, after 1 day, sprayed with an aqueous emulsion spray liquor which comprises 12.5 ppm of active compound, incubated at 25° C. for 6 days and then evaluated. The reduction in the population in percent (% activity) is determined by comparing the number of dead eggs, larvae and adults on the treated and on the untreated plants.

In this test, the compounds of the Tables A1 to A8 and Tables 1 to 48 show good activity. Thus, in particular the compounds A1.1 to A8.1 are more than 80% effective.

What is claimed is:
1. A compound of the formula (I)

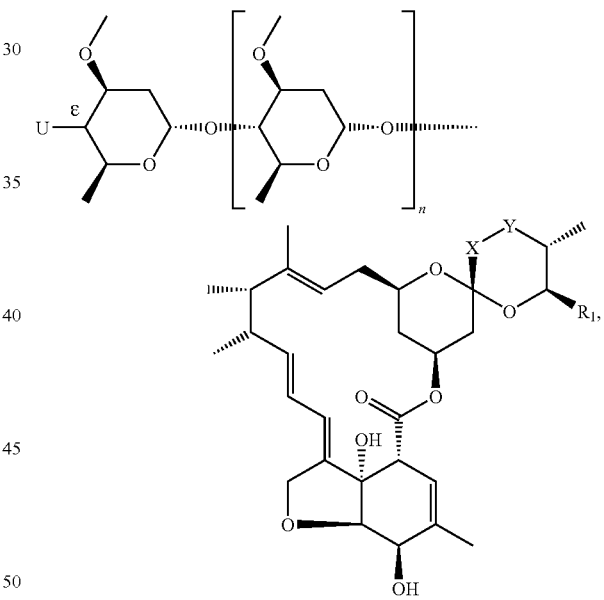

U is $-N(R_2)OR_3$ or $-N^+(O^-)=C(R_E)(R_Z)$;
n is 0 or 1;
X—Y is —CH=CH— or —CH$_2$—CH$_2$—;
R$_1$ is C$_1$-C$_{12}$alkyl, C$_3$-C$_8$cycloalkyl or C$_2$-C$_{12}$alkenyl;
R$_2$ and R$_3$ are, independently from each other, —Q, —C(O)—Z—Q or —CN;
R$_Z$ and R$_E$ are, independently from each other, —Q, —C(O)—Z—Q or —CN; or
R$_Z$ and R$_E$ together are a three- to seven membered alkylene or alkenylene bridge, which is unsubstituted or mono- to tri-substituted;
Z is a bond, O or —NR$_4$—;
R$_4$ is H, C$_1$-C$_8$alkyl, hydroxy-C$_1$-C$_8$alkyl, C$_3$-C$_8$cycloalkyl, C$_2$-C$_8$alkenyl, C$_2$-C$_8$alkynyl, phenyl, benzyl —C(=O)R$_5$, or —CH$_2$—C(=O)—R$_5$;

Q is H, $C_1$-$C_{12}$alkyl, $C_2$-$C_{12}$alkenyl, $C_2$-$C_{12}$alkynyl, $C_3$-$C_{12}$-cycloalkyl, $C_5$-$C_{12}$-cycloalkenyl, aryl, or heterocyclyl, which are unsubstituted or mono- to pentasubstituted; wherein the alkyl-, alkenyl-, alkynyl-, alkylene-, alkenylene-, cycloalkyl-, cycloalkenyl-, aryl- and heterocyclyl-radicals of the substituents Q, $R_2$, $R_3$, $R_4$, $R_Z$, $R_E$ and Q are independently of each other selected from the group consisting of OH, =O, SH, =S, halogen, CN, —N3, SCN, $NO_2$, $Si(C_1$-$C_8$alkyl$)_3$, halo-$C_1$-$C_2$alkyl, $C_1$-$C_2$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_2$-$C_{12}$alkenylthio, $C_2$-$C_{12}$haloalkenylthio, $C_2$-$C_{12}$alkenylsulfinyl, $C_2$-$C_{12}$haloalkenylsulfinyl, $C_2$-$C_{12}$alkenylsulfonyl, $C_2$-$C_{12}$haloalkenylsulfonyl, $C_3$-$C_8$cycloalkyl which is unsubstituted or substituted by one to three methyl groups, norbornylenyl, $C_3$-$C_8$halocycloalkyl, $C_1$-$C_{12}$alkoxy, $C_3$-$C_8$cycloalkoxy, $C_1$-$C_{12}$alkylthio, $C_3$-$C_8$cycloalkylthio, $C_1$-$C_{12}$haloalkylthio, $C_1$-$C_{12}$alkyl-sulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, —N($R_8$)$_2$ wherein the two $R_8$ are independent of each other, —C(=O)$R_5$, —O—C(O)$R_6$, —NHC(O)$R_5$, —S—C(=S)$R_6$, —P(=O)(O$C_1$-$C_6$alkyl)$_2$, —S(=O)$_2R_9$; —NH—S(=O)$_2R_9$, OC(=O)—$C_1$-$C_6$alkyl-S(O)$_2R_9$, aryl, benzyl, heterocyclyl, aryloxy, benzyloxy, heterocyclyloxy, arylthio, benzylthio, heterocyclylthio; wherein the aryl, heterocyclyl, aryloxy, benzyloxy, heterocyclyloxy, arylthio, benzylthio and heterocyclythio radicals are either unsubstituted or, depending on the possibilities of substitution on the ring, mono- to pentasubstituted by substituents selected from the group consisting of OH, halogen, CN, $NO_2$, $C_1$-$C_{12}$alkyl, $C_1$-$C_{12}$haloalkyl, $Si(C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_3$-$C_8$cycloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkyl, $C_2$-$C_8$alkenyl, $C_2$-$C_8$alkynyl, phenoxy, phenyl-$C_1$-$C_6$alkyl, methylene-dioxy, —C(=O)$R_5$, —O—C(=O)—$R_6$, —NH—C(=O)$R_6$, —N($R_8$)$_2$, wherein the two $R_8$ are independent of each other, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

$R_5$ is H, OH, SH, —N($R_8$)$_2$ wherein the two $R_8$ are independent of each other, $C_1$-$C_24$alkyl, $C_2$-$C_{12}$alkenyl, $C_1$-$C_8$hydroxyalkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkyl, $C_1$-$C_6$alkoxy-$C_1$-$C_6$alkoxy, $C_1$-$C_6$alkoxy-$C_1$-$C_6$alkoxy-$C_1$-$C_6$alkyl, $C_1$-$C_{12}$alkylthio, $C_2$-$C_8$alkenyloxy, $C_3$-$C_8$alkynyloxy, $Si(C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, NH—$C_1$-$C_6$alkyl-C(=O)$R_7$, —N($C_1$-$C_6$alkyl)-$C_1$-$C_6$alkyl-C(=O)—$R_7$, —O—$C_1$-$C_2$alkyl-C(=O)$R_7$, —$C_1$-$C_6$alkyl-S(=O)$_2R_9$, aryl, benzyl, heterocyclyl, aryloxy, benzyloxy, heterocyclyloxy; or aryl, benzyl, heterocyclyl, aryloxy, benzyloxy or heterocyclyloxy, which are independently of one another, depending on the substitution possibilities, mono- to trisubstituted in the ring by halogen, nitro, $C_1$-$C_6$alkyl, $C_1$-$C_6$alkoxy, $C_1$-$C_6$haloalkyl or $C_1$-$C_6$haloalkoxy;

$R_6$ is H, $C_1$-$C_{24}$alkyl, $C_1$-$C_{12}$haloalkyl, $C_1$-$C_{12}$hydroxyalkyl, $C_2$-$C_8$alkenyl, $C_2$-$C_8$alkynyl, $C_1$-$C_6$alkoxy-$C_1$-$C_6$alkyl, $Si(C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, (N$R_8$)$_2$, wherein the two $R_8$ are independent of each other, —$C_1$-$C_6$alkyl-C(=O)$R_8$, —$C_1$-$C_6$alkyl-S(=O)$_2R_9$, aryl, benzyl, heterocyclyl; or aryl, benzyl or heterocyclyl which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $Si(C_1$-$C_8$alkyl)$_3$, $C_1$-$C_{12}$alkoxy-$C_1$-$C_12$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy and $C_1$-$C_{12}$halo-alkylthio;

$R_7$ is H, OH, $C_1$-$C_2$4alkyl that is optionally substituted with OH, or —S(O)$_2$—$C_1$-$C_6$alkyl; $C_1$-$C_{12}$alkenyl, $C_2$-$C_{12}$alkynyl, $C_1$-$C_{12}$alkoxy, $C_1$-$C_6$alkoxy-$C_1$-$C_6$alkyl, $C_1$-$C_6$alkoxy-$C_1$-$C_6$alkoxy, $C_2$-$C_8$alkenyloxy, aryl, aryloxy, benzyloxy, heterocyclyl, heterocyclyloxy or —N($R_8$)$_2$, wherein the two $R_8$ are independent of each other;

$R_8$ is H, $C_1$-$C_6$alkyl, which is optionally substituted with one to five substituents selected from the group consisting of halogen, hydroxy, cyano $C_1$-$C_6$alkoxy, =O, $C_2$-$C_{12}$alkenyl, $C_2$-$C_{12}$haloalkenyl, $C_2$-$C_{12}$haloalkynyl and $C_3$-$C_{12}$haloalkynyloxy; $C_3$-$C_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $Si(C_1$-$C_8$alkyl)$_3$, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_1$-$C_{12}$alkylthio and $C_1$-$C_{12}$haloalkylthio;

$R_9$ is H, $C_1$-$C_6$alkyl, which is optionally substituted with one to five substituents selected from the group consisting of halogen, $C_1$-$C_6$alkoxy, OH, =O, $C_2$-$C_{12}$alkenyl, $C_2$-$C_{12}$haloalkenyl, $C_2$-$C_{12}$haloalkynyl, $C_2$-$C_{12}$haloalkynyl and cyano; aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $Si(C_1$-$C_8$alkyl)$_3$, $C_1$-$C_{12}$alkoxy, $C_1$-$C_{12}$alkoxy-$C_1$-$C_{12}$alkoxy, $C_1$-$C_{12}$haloalkoxy, $C_3$-$C_8$cycloalkoxy, $C_2$-$C_{12}$alkenyloxy, $C_2$-$C_{12}$haloalkenyloxy, $C_2$-$C_{12}$haloalkenyl, $C_3$-$C_{12}$alkynyloxy, $C_2$-$C_{12}$haloalkynyl, $C_3$-$C_{12}$haloalkynyloxy, $C_1$-$C_{12}$alkylthio and $C_1$-$C_{12}$haloalkylthio;

or, if appropriate, an E/Z isomer, E/Z isomer mixture and/or tautomer thereof.

2. A pesticide composition which contains at least one compound of the formula (I) as described in claim 1 as active compound and at least one auxiliary.

3. A method for controlling pests comprising applying a composition as described in claim 2 to the pests or a habitat of the pests.

4. A process for preparing a composition as described in claim 2 comprising intimately mixing and/or grinding the active compound with at least one auxiliary.

5. A method for protecting plant propagation material, comprising applying the composition as described in claim 2 to the propagation material or a location where the propagation material is planted.

6. Plant propagation material comprising a composition as described in claim 2.

* * * * *